(12) United States Patent
McHardy et al.

(10) Patent No.: US 7,049,335 B2
(45) Date of Patent: May 23, 2006

(54) 3-AZABICYCLO[3.1.0]HEXANE DERIVATIVES

(75) Inventors: Stanton F. McHardy, Coventry, RI (US); Spiros Liras, Stonington, CT (US); Steven D. Heck, Norwich, CT (US)

(73) Assignee: Pfizer Inc., New York, NY (US)

( * ) Notice: Subject to any disclaimer, the term of this patent is extended or adjusted under 35 U.S.C. 154(b) by 20 days.

(21) Appl. No.: 10/278,142

(22) Filed: Oct. 22, 2002

(65) Prior Publication Data
US 2003/0087898 A1 May 8, 2003

Related U.S. Application Data

(60) Provisional application No. 60/338,511, filed on Oct. 22, 2001.

(51) Int. Cl.
A61K 31/403 (2006.01)
C07D 209/52 (2006.01)

(52) U.S. Cl. ...................... 514/412; 548/515
(58) Field of Classification Search ............... 548/515; 514/412
See application file for complete search history.

(56) References Cited

U.S. PATENT DOCUMENTS

| | | | |
|---|---|---|---|
| 6,313,312 B1* | 11/2001 | Banks et al. | 548/452 |
| 6,610,711 B1 | 8/2003 | Armer et al. | 514/331 |
| 6,812,236 B1 | 11/2004 | Gibson et al. | 514/317 |
| 2002/0025948 A1* | 2/2002 | Banks et al. | 514/79 |
| 2002/0064825 A1 | 5/2002 | Lewis et al. | 435/69.1 |
| 2003/0013875 A1 | 1/2003 | Banks et al. | 544/60 |
| 2003/0087898 A1 | 5/2003 | McHardy et al. | 514/224.2 |
| 2003/0207876 A1* | 11/2003 | Banks et al. | 514/228.2 |
| 2004/0204445 A1 | 10/2004 | Coe et al. | 514/304 |
| 2004/0204453 A1 | 10/2004 | McHardy et al. | 514/317 |
| 2005/0043327 A1 | 2/2005 | Coe et al. | 514/263.22 |
| 2005/0075387 A1 | 4/2005 | Tickner et al. | 514/412 |

FOREIGN PATENT DOCUMENTS

| | | | | |
|---|---|---|---|---|
| EP | 0506468 | 4/1995 | | |
| EP | 0506478 | 9/1997 | | |
| EP | 0287339 | 8/2004 | | |
| WO | WO 0039089 | 7/2000 | | 209/52 |
| WO | WO 0198267 | 12/2001 | | 209/52 |
| WO | WO 03 035622 | 5/2003 | | |
| WO | WO 03 101963 | 12/2003 | | |

OTHER PUBLICATIONS

FDA mulls drug to slow late-stage Alzheimer's [online], [retrieved on Sep. 23, 2003]. Retrieved from the Internet,URL:http://www.cnn.com/2003/HEALTH/conditions/09/24/alzheimers.drug.ap/index.html>.*
U.S. Appl. No. 60/218,500.*

Trayham, J.G. et al. "Effects of Ring Size on the Reactions of Cyclic Olefins Halohydrinsfrom Methylenecycloalkanes" *Tetrahedron*, Elsevier Science Publishers, vol. 7, 1959, pp. 165-172.
Beck, A., et al. "Preparation of Tetrahydrobenzodindoles from 1-Tetralones", Jour. Chem. Society, Perkin Transactions 1, Letchworth GB, 1990, pp. 689-693.
Mosettig, E, et al. "Ring enlargement with diazomethane in the hydro-aromatic series", Journ. Of American Chemical Society, vol. 52, 1930, pp. 3456-3463.
Talukdar, PB et al. "Chemistry of Ehtylenimine. VI. Pyrolysis of 7-acetyl-7azaspiro's 5.2loctane", Journ Organic Chemistry, No. 24, 1959, pp. 526-528.
Piper J.R. "The use of alpha-amino acids in the synthesis of derivatives of 2-aminoethanethiol as potential antiradiaton agents" Jour. of Medicinal Chemistry, vol. 9, 1966, pp. 911-920.
Campbell, M.M., et al. "Spiroheterocylces derived from tetralone", Tetrahedron, vol. 41, No. 23, 1985, pp. 5637-5644.
Mosettig, E, et al. "New alkamines in the tetrahydronapthalene series", Journ. Of American Chemical Society, vol. 53, 1931, pp. 2295-2300.
Zhou, Z. et al., *Biophysical Journal*. "Properties of HERG Channels Stably Expressed in HEK 293 Cells Studied at Physiological Temperature", vol. 74, pp. 230-241 (1998).
Wilkinson, G.R., *New England Journal of Medicine*, "Drug Metabolism and Variability Among Patients In Drug Response", vol. 352, pp. 2211-2221 (2005).

* cited by examiner

*Primary Examiner*—Kamal A. Saeed
*Assistant Examiner*—Rebecca Anderson
(74) *Attorney, Agent, or Firm*—Gregg C. Benson; Arlene K. Musser

(57) ABSTRACT

The subject invention provides a compound of the formula I,

I

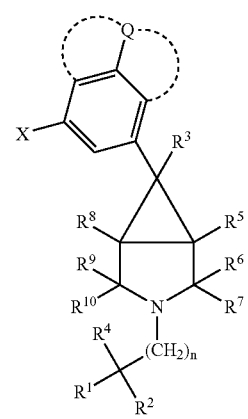

wherein X, Q, n, $R^1$, $R^2$, $R^3$, $R^4$, $R^5$, $R^6$, $R^7$, $R^8$, $R^9$, and $R^{10}$ are as defined. Compounds of formula I have activity as opioid receptor antagonists. The subject invention furthermore provides for pharmaceutical compositions and therapeutic methods comprising compounds of formula I.

8 Claims, No Drawings

3-AZABICYCLO[3.1.0]HEXANE DERIVATIVES

This application claims priority under 35 U.S.C. 119(e) of U.S. Application Ser. No. 60/338,511, filed Oct. 22, 2001.

FIELD OF THE INVENTION

The subject invention relates to 3-azabicyclo[3.1.0]hexane derivatives, pharmaceutical compositions comprising such derivatives and methods of using such derivatives to treat disorders and conditions mediated by an opioid receptor. The subject also particularly relates to using such derivatives to treat certain disorders and conditions, for example irritable bowel syndrome, drug addiction or dependency, including alcohol addiction or dependency, depression, and eating disorders.

BACKGROUND OF THE INVENTION

The compounds of the present invention bind to opiate receptors (e.g. mu, kappa and delta opioid receptors). Compounds that bind to such receptors are likely to be useful in the treatment of diseases modulated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction and dependence, sexual dysfunction, shock, stroke, spinal damage and head trauma.

Certain 4-arylpiperidine-based compounds are disclosed in European patent applications EP 287339, EP 506468 and EP 506478 as opioid antagonists. In addition, International Patent Application WO 95/15327 discloses azabicycloalkane derivatives useful as neuroleptic agents. 3-Azabicyclo[3.1.0] hexane derivatives useful as opioid receptor antagonists are also disclosed in WO 00/39089.

It is furthermore beneficial to obtain drugs, for example drugs that bind to opioid receptors, that are not substrates of the enzyme CYP2D6. The presence of CYP2D6 enzyme among the human population is variable, and therefore it is easier to develop dosage schemes for a drug that are more generally applicable to a human population if the drug is not metabolized by CYP2D6.

SUMMARY OF THE INVENTION

The subject invention provides a compound of the formula I,

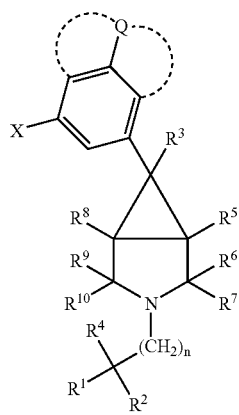

wherein X is H, halogen, —OH, —CN, —$C_1$–$C_4$ alkyl substituted with from one to three halogen atoms, or —O($C_1$–$C_4$ alkyl), wherein the $C_1$–$C_4$ alkyl of —O($C_1$–$C_4$ alkyl) is optionally substituted with from one to three halogen atoms;

Q is halogen, —OH, —O($C_1$–$C_4$ alkyl), —$NH_2$, —NH($C_1$–$C_4$ alkyl), —N($C_1$–$C_4$ alkyl)($C_1$–$C_4$ alkyl), —C(=O)$NH_2$, —C(=O)NH($C_1$–$C_4$ alkyl), —C(=O)N($C_1$–$C_4$ alkyl)($C_1$–$C_4$ alkyl), or —NHS(=O)$_2R^{11}$;

or Q may form a 5 or 6 membered cycloalkyl or heterocycloalkyl ring with either carbon atom adjacent to the carbon atom to which it is attached, thereby forming a bicyclic fused ring system with the phenyl to which it is attached, wherein said heterocycloalkyl comprises from one to three hetero moieties selected from O, S, —C(=O), and N, and wherein said cycloalkyl or heterocycloalkyl optionally contains one or two double bonds;

$R^1$ and $R^2$ are, with the carbon to which they are attached, connected to form a $C_3$–$C_7$ cycloalkyl or a 4–7 membered heterocycloalkyl comprising from one to three hetero moieties selected from O, S, —C(=O), and N; and wherein said cycloalkyl or heterocycloalkyl optionally contains one or two double bonds; and wherein said cycloalkyl or heterocycloalkyl is optionally fused to or substituted with a $C_6$–$C_{14}$ aryl or 5–14 membered heteroaryl group;

wherein said $C_3$–$C_7$ cycloalkyl or 4–7 membered heterocycloalkyl formed by $R^1$ and $R^2$ can each optionally be substituted by from one to three $R^{12}$ groups, and said optionally fused or said substituted aryl or heteroaryl can each optionally independently be substituted with from one to six $R^{12}$ groups, wherein the $R^{12}$ groups are selected from $R^{13}$, $R^{16}$, —$C_1$–$C_4$ alkyl containing one or two unsaturated bonds, halogen, —$OR^{13}$, —$NO_2$, —CN, —$C_3$–$C_6$ cycloalkyl, —$NR^{13}R^{14}$, —$NR^{13}C(=O)R^{14}$, —C(=O)$NR^{13}R^{14}$, —OC(=O)$R^{13}$, —C(=O)$OR^{13}$, —C(=O)$R^{13}$, —$NR^{13}C(=O)OR^{14}$, —$NR^{13}C(=O)NR^{14}R^{15}$, —$NR^{13}S(=O)_2R^{14}$, and —S(=O)$_2R^{13}$;

$R^3$ is $C_1$–$C_4$ alkyl, wherein said $C_1$–$C_4$ alkyl optionally contains one or two unsaturated bonds;

$R^4$ is —$C_1$–$C_4$ alkyl which may optionally contain one or two unsaturated bonds, —OH, —CN, $NO^2$, —$OR^{16}$, —$NH_2$, —$NHR^{16}$, —$NR^{16}R^{17}$, or —NHC(=O)$R^{16}$;

$R^5$ and $R^8$ are each independently H or methyl;

$R^6$, $R^7$, $R^9$ and $R^{10}$ are H;

$R^{11}$ is selected from $C_1$–$C_4$ alkyl, —($C_2$–$C_4$ alkylene)—O—($C_1$–$C_4$ alkyl), 4-(1-methylimidazole), —($C_1$–$C_4$ alkylene)—$NH_2$, —($C_1$–$C_4$ alkylene)—NH($C_1$–$C_4$ alkyl), —($C_1$–$C_4$ alkylene)—N($C_1$–$C_4$ alkyl)($C_1$–$C_4$ alkyl);

each $R^{13}$, $R^{14}$, and $R^{15}$ is independently selected from H, $R^{16}$, $C_1$–$C_4$ alkyl, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —C(=O)($C_1$–$C_4$ alkyl), —C(=O)OH, —C(=O)O($C_1$–$C_4$ alkyl), —NHC(=O)($C_1$–$C_4$ alkyl), —C(=O)$NH_2$, and —C(=O)N($C_1$–$C_4$ alkyl)($C_1$–$C_4$ alkyl), or $R^{13}$ and $R^{14}$ when in —$NR^{13}R^{14}$, may optionally be connected to form a 4 to 6 membered heterocycloalkyl or heteroaryl group, which heterorayl group optionally comprises from 1 to 3 further hetero moieties selected from N, S, O and —C(=O);

each $R^{16}$ and $R^{17}$ is independently selected from $C_6$–$C_{14}$ aryl and 5–14 membered heteroaryl, wherein said heteroaryl comprises from one to three hetero moieties selected from O, S, —C(=O), and N, and wherein said aryl and heteroaryl are optionally substituted with from one to three substituents selected from $C_1$–$C_4$ alkyl optionally containing one or two unsaturated bonds, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —C(=O) ($C_1$–$C_4$ alkyl), —C(=O)OH, —C(=O)O($C_1$–$C_4$ alkyl), —NHC (=O) ($C_1$–$C_4$ alkyl), —C(=O)$NH_2$, and —C(=O)N ($C_1$–$C_4$ alkyl) ($C_1$–$C_4$ alkyl); and n is an integer selected from zero, 1, 2, 3, 4, and 5; and pharmaceutically acceptable salts thereof.

In one embodiment of the invention, compounds of formula I are provided wherein $R^3$ is methyl, ethyl, or straight-chain propyl. In another embodiment, $R^3$ is methyl, ethyl, isopropyl or straight-chain propyl. In a preferred embodiment, $R^3$ is ethyl.

In another embodiment of the invention, compounds of formula I are provided wherein $R^4$ is —CN, —$NO_2$, —OH, —$NH_2$, —O($C_1$–$C_4$ alkyl), —($C_1$–$C_4$ alkylene)-OH, —NHC(=O) ($C_1$–$C_4$ alkyl), —NH($C_1$–$C_4$ alkyl), or —N($C_1$–$C_4$ alkyl)($C_1$–$C_4$ alkyl).

In another embodiment of the invention, compounds of formula I are provided wherein $R^4$ is —CN, —$NO_2$, —OH, —$OCH_3$, —$CH_2OH$, —$NH_2$, or —NHC(=O)$CH_3$. In another embodiment $R^4$ is —OH, —$OCH_3$, —$CH_2OH$, —$NH_2$, or —NHC(=O)$CH_3$. In a preferred embodiment, $R^4$ is —OH.

Q is halogen, —OH, —O($C_1$–$C_4$ alkyl), —$NH_2$, —NH ($C_1$–$C_4$ alkyl), —N($C_1$–$C_4$ alkyl) ($C_1$–$C_4$ alkyl), —C(=O) $NH_2$, —C(=O)NH($C_1$–$C_4$ alkyl), —C(=O)N($C_1$–$C_4$ alkyl) ($C_1$–$C_4$ alkyl), —NHS(=O)$_2$H or —NHS(=O)$_2R^{11}$;

$R^1$ and $R^2$ are, with the carbon to which they are attached, connected to form a $C_3$–$C_7$ cycloalkyl or a 4–7 membered heterocycloalkyl comprising from one to three hetero moieties selected from O, S, —C(=O), and N; and wherein said cycloalkyl or heterocycloalkyl optionally contains one or two double bonds; and wherein said cycloalkyl or heterocycloalkyl is optionally fused to a $C_6$–$C_{14}$ aryl or 5–14 membered heteroaryl group;

wherein said $C_3$–$C_7$ cycloalkyl or 4–7 membered heterocycloalkyl formed by $R^1$ and $R^2$ can each optionally be substituted by from one to three $R^{12}$ groups, and said optionally fused aryl or heteroaryl can each optionally independently be substituted with from one to six $R^{12}$ groups, wherein the $R^{12}$ groups are selected from $R^{13}$, $R^{16}$, —$C_1$–$C_4$ alkyl containing one or two unsaturated bonds, halogen, —$OR^{13}$, —$NO_2$, —CN, —$C_3$–$C_6$ cycloalkyl, —$NR^{13}R^{14}$, —$NR^{13}C$(=O)$R^{14}$, —C(=O)$NR^{13}R^{14}$, —OC (=O)$R^{13}$, —C(=O)$OR^{13}$, —C(=O)$R^{13}$, —$NR^{13}C$(O) $OR^{14}$, —$NR^{13}C$(=O)$NR^{14}R^{15}$, —$NR^{13}S$(=O)$_2R^{14}$, and —S(=O)$_2R^{13}$;

$R^4$ is —$C_1$–$C_4$ alkyl which may optionally contain one or two unsaturated bonds, —OH, —CN, —$NO_2$, —$OR^{16}$, —$NH_2$, —$NHR^{16}$, —$NR^{16}R^{17}$, or —NHC(=O)$R^{16}$;

each $R^{16}$ and $R^{17}$ is independently selected from $C_6$–$C_{14}$ aryl and 5–14 membered heteroaryl, wherein said heteroaryl comprises from one to three hetero moieties selected from O, S, —C(=O), and N, and wherein said aryl and heteroaryl are optionally substituted with from one to three substituents selected from $C_1$–$C_4$ alkyl optionally containing one or two unsaturated bonds, halogen, —OH, —SH, —$NH_2$, —NH ($C_1$–$C_4$ alkyl), —N($C_1$–$C_4$ alkyl) ($C_1$–$C_4$ alkyl), —O($C_1$–$C_4$ alkyl), —S($C_1$–$C_4$ alkyl), —CN, —$NO_2$, —C(=O) ($C_1$–$C_4$ alkyl), —C(=O)OH, —C(=O)O($C_1$–$C_4$ alkyl), —NHC (=O) ($C_1$–$C_4$ alkyl), —C(=O)$NH_2$, and —C(=O)N ($C_1$–$C_4$ alkyl) ($C_1$–$C_4$ alkyl); and In another embodiment of the invention, compounds of formula I are provided wherein Q is halogen, —OH, —O($C_1$–$C_4$ alkyl), —$NH_2$, —NH($C_1$–$C_4$ alkyl), —N($C_1$–$C_4$ alkyl) ($C_1$–$C_4$ alkyl), —C(=O)$NH_2$, —C(=O)NH($C_1$–$C_4$ alkyl), —C(=O)N($C_1$–$C_4$ alkyl)($C_1$–$C_4$ alkyl), —NHS (=O)$_2$H, or —NHS(=O)$_2R^{11}$.

In another embodiment of the invention, compounds of formula I are provided wherein Q is F, —OH, —C(=O) $NH_2$, —NHS(=O)$_2CH_3$, —NHS(=O)$_2CH_2CH_3$, —NHS (=O)$_2CH_2CH_2CH_3$, —NHS(=O)$_2CH(CH_3)(CH_3)$, —NHS(=O)$_2CH_2CH_2OCH_3$, or —NHS(=O)$_2$(4-(1-methylimidazole)). In another embodiment, Q is F, —OH, —C(=O)$NH_2$, —NHS(=O)$_2CH_3$, —NHS(=O)$_2$ $CH_2CH_2OCH_3$, or —NHS(=O)$_2$(4-(1-methylimidazole)).

In another embodiment of the invention, compounds of formula I are provided, wherein X is H, F, —OH, —C(=O) $NH_2$, or —CN. In another embodiment, X is H, F, —OH, or —CN.

In another embodiment of the invention, Q is F, —OH, —C(=O)$NH_2$, —NHS(=O)$_2CH_3$, —NHS(=O)$_2$ $CH_2CH_2OCH_3$, or —NHS(=O)$_2$(4-1-methylimidazole)) and X is H, F, —OH, or —CN.

In another embodiment of the invention, compounds of formula I are provided, wherein n is an integer selected from zero, one, two, or three. Preferably, n is an integer selected from one, two or three.

In another embodiment of the invention, compounds of formula I are provided, wherein $R^1$ and $R^2$, with the carbon to which they are attached, are connected to form a cyclopropyl, cyclobutyl, cyclopentyl, or cyclohexyl group, each optionally substituted with one or two $R^{12}$ groups.

In another embodiment of the invention, compounds of formula I are provided, wherein $R^1$ and $R^2$, with the carbon to which they are attached, are connected to form a cyclopentyl group, optionally substituted with from one or two $R^{12}$ groups. In one embodiment, the cyclopentyl group formed by $R^1$ and $R^2$ is not substituted with an $R^{12}$ group.

In another embodiment of the invention, compounds of formula I are provided wherein $R^1$ and $R^2$, with the carbon to which they are attached, are connected to form a cyclohexyl group optionally substituted with one or two $R^{12}$ groups. In one embodiment, the cyclohexyl group formed by $R^1$ and $R^2$ is not substituted with an $R^{12}$ group.

In another embodiment of the invention, the ring formed by $R^1$ and $R^2$, for example a cyclopentyl or cyclohexyl ring, is fused to a benzene ring, and the ring formed by $R^1$ and $R^2$ and the benzene ring are each optionally substituted as recited above. In a more specific embodiment, the benzene ring and/or the ring formed by $R^1$ and $R^2$ are each optionally substituted with one or two $R^{12}$ groups. In one embodiment, the benzene is not substituted with any $R^{12}$ group. In another more specific embodiment, $R^1$ and $R^2$ form a cyclohexyl group, which cyclohexyl group is fused to a benzene ring, or $R^1$ and $R^2$ form a cyclopentyl group, which cyclopentyl group is fused to a benzene ring. In either case (cylopentyl fused to benzene or cyclohexyl fused to benzene) said cyclopentyl or cyclohexyl and/or the fused benzene ring are each optionally substituted with one or two $R^{12}$ as recited above. In another embodiment, the cyclohexyl or cyclopentyl group that is fused to the benzene is not substituted with any $R^{12}$ group.

In each of the aforementioned embodiments, when an $R^{12}$ substituent is present, it is in one embodiment a —CN or halogen, for example a fluoro group.

In another embodiment of the invention, when $R^1$ and $R^2$ form a cyclohexyl or cyclopentyl, the cyclohexyl or cyclopentyl are optionally fused to a benzene ring, and $R^3$ is methyl, ethyl, isopropyl or straight-chain propyl. In another such embodiment $R^3$ is methyl, ethyl or straight-chain propyl. In a preferred embodiment, $R^3$ is ethyl.

In another embodiment of the invention, when $R^1$ and $R^2$ form a cyclohexyl or cyclopentyl, the cyclohexyl or cyclopentyl are optionally fused to a benzene ring, and $R^4$ is —OH, —OCH₃, —CH₂OH, —NH₂, or —NHC(=O)CH₃. In another such embodiment R⁴ is —CN, —NO₂, —OH, —OCH₃, —CH₂OH, —NH₂, or —NHC(=O)CH₃. In another such embodiment R⁴ is —CN, —NO₂, —OH, —NH₂, —O(C₁–C₄ alkyl), —(C₁–C₄ alkylene)-OH, —NHC(=O)(C₁–C₄ alkyl), —NH(C₁–C₄ alkyl), or —N(C₁–C₄ alkyl)(C₁–C₄ alkyl). In a preferred embodiment, R⁴ is —OH.

In another embodiment of the invention, when R¹ and R² form a cyclohexyl or cyclopentyl, the cyclohexyl or cyclopentyl are optionally fused to a benzene ring, and Q is F, —OH, —C(=O)NH₂, —NHS(=O)₂CH₃, —NHS(=O)₂CH₂CH₂OCH₃, or —NHS(=O)₂(4-(1-methylimidazole)). In another such embodiment Q is halogen, —OH, —O(C₁–C₄ alkyl), —NH₂, —NH(C₁–C₄ alkyl), —N(C₁–C₄ alkyl)(C₁–C₄ alkyl), —C(=O)NH₂, —C(=O)NH(C₁–C₄ alkyl), —C(=O)N(C₁–C₄ alkyl)(C₁–C₄ alkyl), —NHS(=O)₂H, or —NHS(=O)₂R¹¹. In another such embodiment, Q is F, —OH, —C(=O)NH₂, —NHS(=O)₂CH₃, —NHS(=O)₂CH₂CH₃, —NHS(=O)₂CH₂CH₂CH₃, —NHS(=O)₂CH(CH₃)(CH₃), —NHS(=O)₂CH₂CH₂OCH₃, or —NHS(=O)₂(4-(1 -methylimidazole)).

In another embodiment of the invention, when R¹ and R² form a cyclohexyl or cyclopentyl, the cyclohexyl or cyclopentyl are optionally fused to a benzene ring, and X is H, F, —OH, —C(=O)NH₂, or —CN. In another such embodiment, X is H, F, —OH, or —CN.

In another embodiment of the invention, when R¹ and R² form a cyclohexyl or cyclopentyl, the cyclohexyl or cyclopentyl are optionally fused to a benzene ring, Q is F, —OH, —C(=O)NH₂, —NHS(=O)₂CH₃, —NHS(=O)₂CH₂CH₂OCH₃, or —NHS(=O)₂(4-1-methylimidazole)) and X is H, F, —OH, or —CN.

In another embodiment of the invention, when R¹ and R² form a cyclohexyl or cyclopentyl, the cyclohexyl or cyclopentyl are optionally fused to a benzene ring, and n is an integer selected from one, two, and three. In another such embodiment, n is an integer selected from one, two, and three, and Q is halogen, —OH, —O(C₁–C₄ alkyl), —NH₂, —NH(C₁–C₄ alkyl), —N(C₁–C₄ alkyl)(C₁–C₄ alkyl), —C(=O)NH₂, —C(=O)NH(C₁–C₄ alkyl), —C(=O)N(C₁–C₄ alkyl) (C₁–C₄ alkyl), —NHS(=O)₂H, or —NHS(=O)₂R¹¹.

In another embodiment of the invention, compounds of formula I are provided wherein R⁵ and R⁸ are both hydrogen.

Specific examples of compounds of the invention of formula I are:

Exo-N-(3-{6-ethyl-3-[3-(1-hydroxy-cyclohexyl)-propyl]-3-aza-bicyclo[3.1.0]hex-6-yl}-phenyl)-methanesulfonamide;

Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide;

Exo-1-{3-[6-(3,5-difluoro-phenyl)-6-ethyl-3-aza-bicyclo[3.1.0]hex-3-yl]-propyl}-cyclohexanol;

Exo-3-{6-ethyl-3-[3-(1-hydroxy-cyclohexyl)-propyl]-3-aza-bicyclo[3.1.0]hex-6-yl}-benzamide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide;

Exo-3-[6-ethyl-3-(2-hydroxy-indan-2-ylmethyl)-3-aza-bicyclo[3.1.0]hex-6-yl]-5-fluoro-benzamide;

Exo-3-[6-ethyl-3-(2-hydroxy-indan-2-ylmethyl)-3-aza-bicyclo[3.1.0]hex-6-yl]-benzamide;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-2-methoxy-ethanesulfonic acid [3-(6-ethyl-3-indan-2-ylmethyl-3-aza-bicyclo[3.1.0]hex-6-yl)-phenyl]-amide;

Exo-N-{3-[6-ethyl-3-(2-hydroxy-indan-2-ylmethyl)-3-aza-bicyclo[3.1.0]hex-6-yl]-5-fluoro-phenyl}-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-1-methyl-1H-imidazole-4-sulfonic acid {3-[6-ethyl-3-(2-hydroxy-indan-2-ylmethyl)-3-aza-bicyclo[3.1.0]hex-6-yl]-phenyl}-amide;

Exo-3-(6-ethyl-3-indan-2-ylmethyl-3-aza-bicyclo[3.1.0]hex-6-yl)-benzamide;

Exo-1-methyl-1H-imidazole-4-sulfonic acid [3-(6-ethyl-3-indan-2-ylmethyl-3-aza-bicyclo[3.1.0]hex-6-yl)-phenyl]-amide;

Exo-3-{6-ethyl-3-[3-(1-hydroxy-cyclohexyl)-propyl]-3-aza-bicyclo[3.1.0]hex-6-yl}-5-fluoro-benzamide;

Exo-1-methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide;

Exo-3-{6-ethyl-3-[3-(1-hydroxy-cyclohexyl)-propyl]-3-aza-bicyclo[3.1.0]hex-6-yl}-phenol;

Exo-2-[6-ethyl-6-(3-hydroxy-phenyl)-3-aza-bicyclo[3.1.0]hex-3-ylmethyl]-indan-2-ol; and Exo-3-(6-ethyl-3-indan-2-ylmethyl-3-aza-bicyclo[3.1.0]hex-6-yl)-phenol;

and pharmaceutically acceptable salts thereof.

Other specific examples of compounds of the invention of formula I are:

Exo-N-(3-{6-ethyl-3-[3-(1-hydroxy-cyclohexyl)-propyl]-3-aza-bicyclo[3.1.0]hex-6-yl}-phenyl)-methanesulfonamide citrate;

Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-1-{3-[6-(3,5-difluoro-phenyl)-6-ethyl-3-aza-bicyclo[3.1.0]hex-3-yl]-propyl}-cyclohexanol;

Exo-3-{6-ethyl-3-[3-(1-hydroxy-cyclohexyl)-propyl]-3-aza-bicyclo[3.1.0]hex-6yl}-benzamide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide citrate;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide besylate;

Exo-3-{6-ethyl-3-[3-(1-hydroxy-cyclohexyl)-propyl]-3-aza-bicyclo[3.1.0]hex-6-yl}-5-fluoro-benzamide;

Exo-3-{6-ethyl-3-[3-(1-hydroxy-cyclohexyl)-propyl]-3-aza-bicyclo[3.1.0]hex-6-yl}-5-fluoro-benzamide tosylate;

Exo-1-methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide;

Exo-1-methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide citrate;

Exo-3-{6-ethyl-3-[3-(1-hydroxy-cyclohexyl)-propyl]-3-aza-bicyclo[3.1.0]hex-6-yl}-phenol;

Exo-3-{6-ethyl-3-[3-(1-hydroxy-cyclohexyl)-propyl]-3-aza-bicyclo[3.1.0]hex-6-yl}-phenol citrate;

Exo-3-[6-ethyl-3-(2-hydroxy-indan-2-ylmethyl)-3-aza-bicyclo[3.1.0]hex-6-yl]-5-fluoro-benzamide;

Exo-N-{3-[6-ethyl-3-(2-hydroxy-indan-2-ylmethyl)-3-aza-bicyclo[3.1.0]hex-6-yl]-phenyl}-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide mesylate;

Exo-3-[6-ethyl-3-(2-hydroxy-indan-2-ylmethyl)-3-aza-bicyclo[3.1.0]hex-6-yl]-benzamide;

Exo-3-[6-ethyl-3-(2-hydroxy-indan-2-ylmethyl)-3-aza-bicyclo[3.1.0]hex-6-yl]-benzamide citrate;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-N-{3-[6-ethyl-3-(2-hydroxy-indan-2-ylmethyl)-3-aza-bicyclo[3.1.0]hex-6-yl]-5-fluoro-phenyl}-methanesulfonamide;

Exo-1-methyl-1H-imidazole-4-sulfonic acid {3-[6-ethyl-3-(2-hydroxy-indan-2-ylmethyl)-3-aza-bicyclo[3.1.0]hex-6-yl]-phenyl}-amide;

Exo-2-[6-ethyl-6-(3-hydroxy-phenyl)-3-aza-bicyclo[3.1.0]hex-3-ylmethyl]-indan-2-ol;

Exo-2-methoxy-ethanesulfonic acid [3-(6-ethyl-3-indan-2-ylmethyl-3-aza-bicyclo[3.1.0]hex-6-yl)-phenyl]-amide;

Exo-3-(6-ethyl-3-indan-2-ylmethyl-3-aza-bicyclo[3.1.0]hex-6-yl)-benzamide;

Exo-1-methyl-1H-imidazole-4-sulfonic acid [3-(6-ethyl-3-indan-2-ylmethyl-3-aza-bicyclo[3.1.0]hex-6-yl)-phenyl]-amide; and Exo-3-(6-ethyl-3-indan-2-ylmethyl-3-aza-bicyclo[3.1.0]hex-6-yl)-phenol.

Preferred compounds of formula I of the invention are:

Exo-N-(3-{6-ethyl-3-[3-(1-hydroxy-cyclohexyl)-propyl]-3-aza-bicyclo[3.1.0]hex-6-yl}-phenyl)-methanesulfonamide;

Exo-N-(3-{6-ethyl-3-[3-(1-hydroxy-cyclohexyl)-propyl]-3-aza-bicyclo[3.1.0]hex-6-yl}-phenyl)-methanesulfonamide citrate Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide besylate;

Exo-3-{6-ethyl-3-[3-(1-hydroxy-cyclohexyl)-propyl]-3-aza-bicyclo[3.1.0]hex-6-yl}-5-fluoro-benzamide;

Exo-3-{6-ethyl-3-[3-(1-hydroxy-cyclohexyl)-propyl]-3-aza-bicyclo[3.1.0]hex-6-yl}-5-fluoro-benzamide tosylate;

Exo-N-{3-[6-ethyl-3-(2-hydroxy-indan-2-ylmethyl)-3-aza-bicyclo[3.1.0]hex-6-yl]-phenyl}-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide mesylate;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide;

Exo-3-[6-ethyl-3-(2-hydroxy-indan-2-ylmethyl)-3-aza-bicyclo[3.1.0]hex-6-yl]-benzamide;

Exo-3-[6-ethyl-3-(2-hydroxy-indan-2-ylmethyl)-3-aza-bicyclo[3.1.0]hex-6-yl]-benzamide citrate;

Exo-3-{6-ethyl-3-[3-(1-hydroxy-cyclohexyl)-propyl]-3-aza-bicyclo[3.1.0]hex-6-yl}-phenol;

Exo-3-{6-ethyl-3-[3-(1-hydroxy-cyclohexyl)-propyl]-3-aza-bicyclo[3.1.0]hex-6-yl}-phenol citrate;

Exo-2-[6-ethyl-6-(3-hydroxy-phenyl)-3-aza-bicyclo[3.1.0]hex-3-ylmethyl]-indan-2-ol Exo-3-{6-Ethyl-3-[2-(2-hydroxy-indan-2-yl)-ethyl]-3-aza-bicyclo[3.1.0]hex-6-yl}-benzamide;

(+/−)-exo-2-Methoxy-ethanesulfonic acid {3-[6-ethyl-3-(2-hydroxy-1,2,3,4-tetrahydro-naphthalen-2-ylmethyl)-3-aza-bicyclo[3.1.0]hex-6-yl]-phenyl}-amide;

(+)-exo-N-{3-[6-Ethyl-3-(2-hydroxy-1,2,3,4-tetrahydro-naphthalen-2-ylmethyl )-3-aza-bicyclo[3.1.0]hex-6-yl]-phenyl}-methanesulfonamide;

(−)-exo-N-{3-[6-Ethyl-3-(2-hydroxy-1,2,3,4-tetrahydro-naphthalen-2-ylmethyl )-3-aza-bicyclo[3.1.0]hex-6-yl]-phenyl}-methanesulfonamide;

Exo-3-[3-(2-Hydroxy-indan-2-ylmethyl)-6-propyl-3-aza-bicyclo[3.1.0]hex-6-yl]-benzamide;

Exo-3-{3-[3-(1-Hydroxy-cyclohexyl)-propyl]-6-propyl-3-aza-bicyclo[3.1.0]hex-6-yl}-benzamide;

Exo-N-(3-{3-[3-(1Cyano-cyclohexyl)-propyl]-6-ethyl-3-aza-bicyclo[3.1.0]hex-6-yl}-phenyl)-methanesulfonamide;

Exo-2-Methoxy-ethanesulfonic acid {3-[3-(2-hydroxy-indan-2-ylmethyl)-6-propyl-3-aza-bicyclo[3.1.0]hex-6-yl]-phenyl}-amide;

Exo-N-{3-[3-(2-Hydroxy-indan-2-ylmethyl)-6-isopropyl-3-aza-bicyclo[3.1.0]hex-6-yl]-phenyl}-methanesulfonamide;

Exo-2-Methoxy-ethanesulfonic acid (3-{3-[3-(1-hydroxy-cyclohexyl)-propyl]-6-isopropyl-3-aza-bicyclo[3.1.0]hex-6-yl}-phenyl)-amide;

Exo-N-{3-[6-Ethyl-3-(cis-1-hydroxy-3-phenyl-cyclobutylmethyl)-3-aza-bicyclo[3.1.0]hex-6-yl]-phenyl}-methanesulfonamide;

Exo-3-[6-Ethyl-3-(cis-1-hydroxy-3-phenyl-cyclobutylmethyl)-3-aza-bicyclo[3.1.0]hex-6-yl]-benzamide;

Exo-Ethanesulfonic acid {3-[6-ethyl-3-(2-hydroxy-indan-2-ylmethyl)-3-aza-bicyclo[3.1.0]hex-6-yl]-phenyl}-amide; and Exo-Ethanesulfonic acid (3-{6-ethyl-3-[3-(1-hydroxy-cyclohexyl)-propyl]-3-aza-bicyclo[3.1.0]hex-6-yl}-phenyl)-amide;

and, of the above compounds that are not salt forms, pharmaceutically acceptable salts thereof.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "aryl", as used herein, unless otherwise indicated, includes an organic radical derived from an aromatic hydrocarbon by removal of one hydrogen, such as phenyl, naphthyl, indenyl, and fluorenyl.

"Heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

Salts of compounds of formula I can be obtained by forming salts with any acidic or basic group present on a compound of formula I. Examples of pharmaceutically acceptable salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium.

The compounds of formula I may have optical centers and therefore may occur in different enantiomeric and other stereoisomeric configurations. The invention includes all enantiomers, diastereomers, and other stereoisomers of such compounds of formula I, as well as racemic and other mixtures thereof.

The synthetic methods described below in the "Detailed Description" section and in Examples produce primarily compounds of formula I having the relative stereochemistry illustrated by compounds of formula II below:

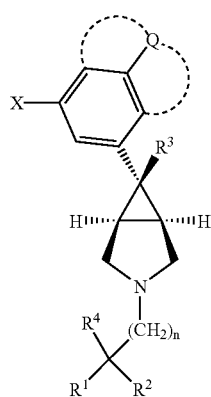

II wherein $R^{1-4}$, Q, X, and n are as defined above. Compounds of formula II, and their pharmaceutically acceptable salts, are preferred embodiments of the invention. Compounds of formula II are exo diastereomers relative to the quarternary carbon on the fused cyclopropane-pyrrolidine ring system. In other words, the phenyl (having Q and X attached thereto) of compounds of formula II is on the exo face of the [3.1.0]-bicyclopyrrolidine moiety.

Compounds of formula II wherein Q is halogen, —OH, —O($C_1$–$C_4$ alkyl), —$NH_2$, —NH($C_1$–$C_4$ alkyl), —N($C_1$–$C_4$ alkyl) ($C_1$–$C_4$ alkyl), —C(=O)$NH_2$, —C(=O)NH($C_1$–$C_4$ alkyl), —C(=O)N($C_1$–$C_4$ alkyl) ($C_1$–$C_4$ alkyl), —NHS(=O)$_2$H, or —NHS(=O)$_2R^{11}$ are preferred.

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention can generally be prepared by carrying out the procedures disclosed in the Schemes and/or in the Examples below, by substituting a readily available isotopically labeled reagent for a non-isotopically labeled reagent.

The subject invention also provides compounds of the formula

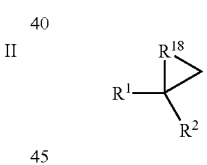

XXI wherein $R^1$ and $R^2$ are, with the carbon to which they are attached, connected to form a $C_5$–$C_7$ cycloalkyl or $C_5$–$C_7$ heterocycloalkyl comprising from one to three hetero atoms selected from O, S, —C(=O), and N; and wherein said cycloalkyl or heterocycloalkyl optionally contains one or two double bonds; and wherein said cycloalkyl or heterocycloalkyl is optionally fused to a $C_6$–$C_{14}$ aryl or $C_5$–$C_{14}$ heteroaryl group;

wherein said $C_5$–$C_7$ cycloalkyl or $C_5$–$C_7$ heterocycloalkyl formed by $R^1$ and $R^2$ can each optionally be substituted by from one to three $R^{12}$ groups, and said optionally fused aryl or heteroaryl can each optionally independently be substituted with from one to six $R^{12}$ groups, wherein the $R^{12}$ groups are selected from $R^{13}$, halogen, —$OR^{13}$, —$NO_2$, —CN, —$C_3$–$C_6$ cycloalkyl, —$NR^{13}R^{14}$, —$NR^{13}$C(=O)$R^{14}$, —C(=O)$NR^{13}R^{14}$, —OC(=O)$R^{13}$, —C(=O)$OR^{13}$, —C(=O)$R^{13}$, —$NR^{13}$C(=O)$OR^{14}$, —$NR^{13}$C(=O)$NR^{14}R^{15}$, —$NR^{13}$S(=O)$_2R^{14}$, and —S(=O)$_2R^{13}$;

each $R^{13}$, $R^{14}$, and $R^{15}$ is independently selected from H and $C_1$–$C_4$ alkyl, wherein each $C_1$–$C_4$ alkyl is optionally substituted with from one to three substituents selected from halogen, —OH, —SH, —NH$_2$, —NH(C$_1$–C$_4$ alkyl), —N(C$_1$–C$_4$ alkyl)(C$_1$–C$_4$ alkyl), —O(C$_1$–C$_4$ alkyl), —S(C$_1$–C$_4$ alkyl), —CN, —NO$_2$, —C(=O)(C$_1$–C$_4$ alkyl), —C(=O)OH, —C(=O)O(C$_1$–C$_4$ alkyl), —NHC(=O)(C$_1$–C$_4$ alkyl), —C(=O)NH$_2$, and —C(=O)N(C$_1$–C$_4$ alkyl) (C$_1$–C$_4$ alkyl); and R$^{18}$ is —O— or —NH—.

Compounds of formula XXI are useful in preparing compounds of formula I.

The subject invention also provides compounds of the formula

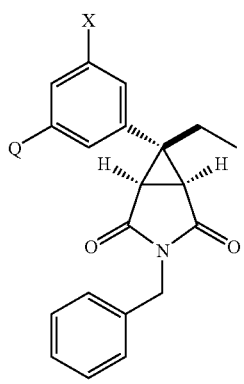

(IV)

wherein X is H, halogen, —OH, —CN, —C$_1$–C$_4$ alkyl substituted with from one to three halogen atoms, or —O(C$_1$–C$_4$ alkyl), wherein the C$_1$–C$_4$ alkyl of —O(C$_1$–C$_4$ alkyl) is optionally substituted with from one to three halogen atoms; and Q is halogen, —OH, —O(C$_1$–C$_4$ alkyl), —NH$_2$, —NH(C$_1$–C$_4$ alkyl), —N(C$_1$–C$_4$ alkyl) (C$_1$–C$_4$ alkyl), —C(=O)NH$_2$, —C(=O)NH(C$_1$–C$_4$ alkyl), —C(=O)N(C$_1$–C$_4$ alkyl) (C$_1$–C$_4$ alkyl), —NHS(=O)$_2$H, or —NHS(=O)$_2$R$^{11}$.

Compounds of formula IV are useful in the preparation of compounds of formula I.

The compounds of the invention of formula I are useful because they possess pharmacological activity in animals, especially mammals, including humans.

The subject invention thus also provides a method for treating in a mammal, including a human, in need thereof a disorder or condition mediated by an opioid receptor or receptors which method comprises administering to said mammal an amount of a compound according to formula I effective in inhibiting an opioid receptor or receptors.

The subject invention also provides a method for treating in a mammal, including a human, in need thereof a disorder or condition mediated by an opioid receptor or receptors which method comprises administering to said mammal an amount of a compound according to claim 1 effective in treating said disorder or condition.

The subject invention also provides a method for treating in a mammal, including a human, in need thereof a disorder or condition selected from irritable bowel syndrome; constipation; nausea; vomiting; pruritic dermatoses, including allergic dermatitis and contact dermatitis; psoriasis; eczema; an insect bite; an eating disorder, including anorexia, bulimia, and obesity; depression, smoking addiction; drug addiction, including alcohol addiction, amphetamine addiction, cocaine addiction and addiction to an opiate, for example morphine, opium, or heroine; an opiate overdose; a sexual dysfunction, including erectile dysfunction and impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I effective in inhibiting an opioid receptor or receptors.

The subject invention also provides a method for treating in a mammal, including a human, in need thereof a disorder or condition selected from irritable bowel syndrome; constipation; nausea; vomiting; pruritic dermatoses, including allergic dermatitis and contact dermatitis; psoriasis; eczema; an insect bite; an eating disorder, including anorexia, bulimia, and obesity; depression, smoking addiction; drug addiction, including alcohol addiction, amphetamine addiction, cocaine addiction and addiction to an opiate, for example morphine, opium, or heroine; an opiate overdose; a sexual dysfunction, including erectile dysfunction and impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I effective in treating said disorder or condition.

The subject invention also provides a pharmaceutical composition for treating in a mammal, including a human, in need thereof a disorder or condition mediated by an opioid receptor or receptors which composition comprises an amount of a compound according to formula I effective in inhibiting an opioid receptor or receptors and a pharmaceutically acceptable carrier.

The subject invention also provides a pharmaceutical composition for treating in a mammal, including a human, in need thereof a disorder or condition mediated by an opioid receptor or receptors which composition comprises an amount of a compound according to formula I effective in treating said disorder or condition and a pharmaceutically acceptable carrier.

The subject invention also provides a pharmaceutical composition for treating in a mammal, including a human, in need thereof a disorder or condition selected from irritable bowel syndrome; constipation; nausea; vomiting; pruritic dermatoses, including allergic dermatitis and contact dermatitis; psoriasis; eczema; an insect bite; an eating disorder, including anorexia, bulimia, and obesity; depression, smoking addiction; drug addiction, including alcohol addiction, amphetamine addiction, cocaine addiction and addiction to an opiate, for example morphine, opium, or heroine; an opiate overdose; a sexual dysfunction, including erectile dysfunction and impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I effective in inhibiting an opioid receptor or receptors and a pharmaceutically acceptable carrier.

The subject invention also provides a pharmaceutical composition for treating in a mammal, including a human, in need thereof a disorder or condition selected from irritable bowel syndrome; constipation; nausea; vomiting; pruritic dermatoses, including allergic dermatitis and contact dermatitis; psoriasis; eczema; an insect bite; an eating disorder, including anorexia, bulimia, and obesity; depression, smoking addiction; drug addiction, including alcohol addiction, amphetamine addiction, cocaine addiction and addiction to an opiate, for example morphine, opium, or heroine; an opiate overdose; a sexual dysfunction, including erectile dysfunction and impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I effective in treating said disorder or condition and a pharmaceutically acceptable carrier.

The terms "treatment", "treating", and the like, refers to reversing, alleviating, or inhibiting the progress of the disorder or condition to which such term applies, or one or more symptoms of such disorder or condition. As used herein, these terms also encompass, depending on the condition of the patient, preventing the onset of a disorder or condition, or of symptoms associated with a disorder or condition, including reducing the severity of a disorder or condition or symptoms associated therewith prior to affliction with said disorder or condition. Thus, "treatment", as used herein, can refer to administration of a compound of the invention to a subject that is not at the time of administration afflicted with the disorder or condition. "Treating" thus also encompasses preventing the recurrence of a disorder or condition or of symptoms associated therewith.

"Mammal", as used herein, and unless otherwise indicated, means any mammal. The term "mammal" includes, for example and without limitation, dogs, cats, and humans.

References herein to disorders and conditions "mediated by an opioid receptor or receptors" indicate disorders or conditions that are caused at least in part by binding of the endogenous ligands to an opioid receptor, for example endogenous ligand binding to a mu, kappa, and/or delta opioid receptor. Examples of disorders and conditions that are mediated by an opioid receptor or receptors include, but are not limited to, irritable bowel syndrome, eating disorders, sexual dysfunction, depression, smoking and drug addictions, as well as the other specific disorders and conditions recited above.

DETAILED DESCRIPTION OF THE INVENTION

Compounds of the formula I, above, and their pharmaceutically acceptable salts, can be prepared according to the following reaction Schemes I through VIII as discussed. Unless otherwise indicated Q, X, n, and $R^1$ through $R^{15}$ are as defined above. Isolation and purification of the products is accomplished by standard procedures which are known to a chemist of ordinary skill.

As used herein, the expression "reaction inert solvent" refers to a solvent system in which the components do not interact with starting materials, reagents, or intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective groups in Organic Chemistry,* John Wiley & Sons, 1981; and T. W. Greene and P. G. M. Wuts, *Protective Groups in Organic Chemistry,* John Wiley & Sons, 1991.

Scheme I illustrates a method for the preparation of compounds having the basic structure of formula I, where X=H, F, Cl, Br, Q=F, Cl, Br, $NO_2$, $OCH_3$, $R^3$=ethyl, $R^5$, $R^8$=hydrogen, $R^6$, $R^7$, $R^9$, $R^{10}$=C=O, and $R^1$, $R^2$ and $R^4$ are described as above.

Referring to Scheme I, a ketone of formula (II) can be treated with hydrazine in an alcoholic solvent such as methanol, at temperatures ranging from room temperature to about the reflux temperature, preferably at about the reflux temperature to produce the desired hydrazone of formula (III). Oxidation of a hydrazone of formula (III) with a suitable oxidant such as $MnO_2$, in solvents such as dioxane or tetrahydrofuran at room temperature produces an intermediate diazonium ion (not depicted). Treatment of this intermediate with a maleimide reagent, such as N-benzylmaleimide in dioxane, at temperatures ranging from room temperature to about the reflux temperature, preferably at about the reflux temperature, produces the desired compound of formula (IV).

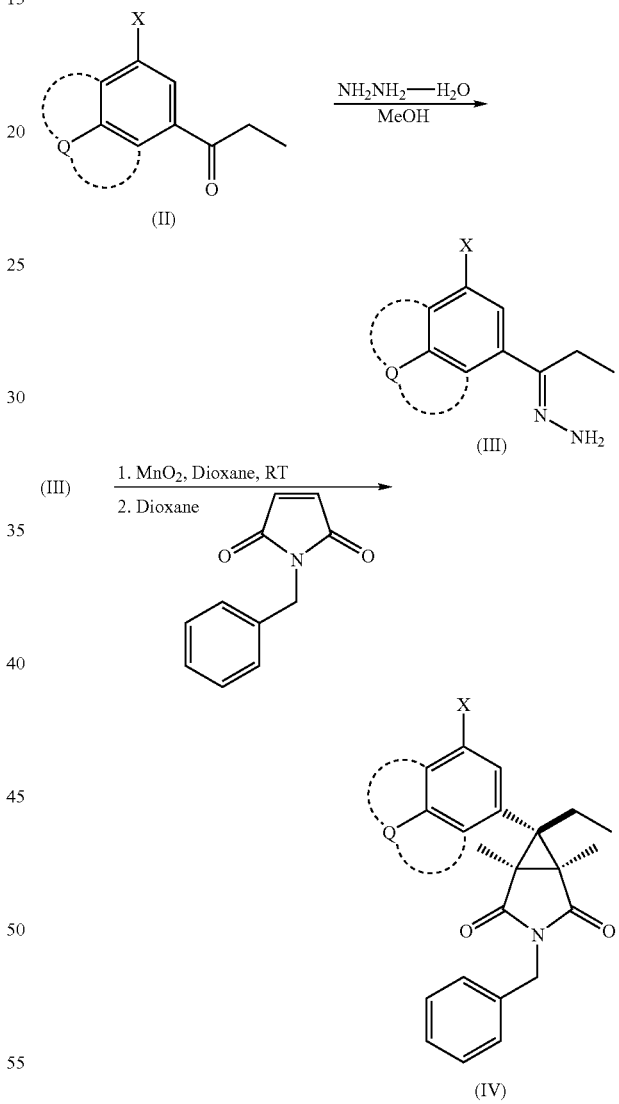

Schemes II–VI below illustrate methods for the preparation of compounds having the basic structure of formula I, where X=H, F, Br, Q=$NHSO_2R^{11}$, F, Br, CN, $CONH_2$, $OCH_3$, OH, $R^3$=ethyl, $R^5$, $R^8$, $R^6$, $R^7$, $R^9$, $R^{10}$=hydrogen, and $R^1$, $R^2$ and $R^4$ are described as above.

Referring to Scheme II, treatment of a compound of formula (V) with hydrogen gas (at pressures ranging from atmospheric to 50 psi) in the presence of a suitable catalyst such as palladium on carbon, in solvents such as ethyl acetate, at temperatures ranging from room temperature to 60° C., preferably at about 60° C., produces the compound of formula (VI). Treatment of an aniline of formula (VI) with an appropriately substituted sulfonyl chloride, such as methanesulfonyl chloride, in the presence of a suitable base, such as pyridine or triethyl amine, in a solvent such as ethyl acetate, at temperatures ranging from 0° C. to room temperature, preferably at about room temperature, produces the desired sulfonamide of formula (VII). Treatment of a compound of formula (VII) with a reducing agent, such as sodium borohydride, in the presence of boron trifluoride diethyl etherate, in solvents such as ethyl ether or tetrahydrofuran, at temperatures ranging from room temperature, to about the reflux temperature, preferably at about the reflux temperature, produces the desired compound of formula (VIII).

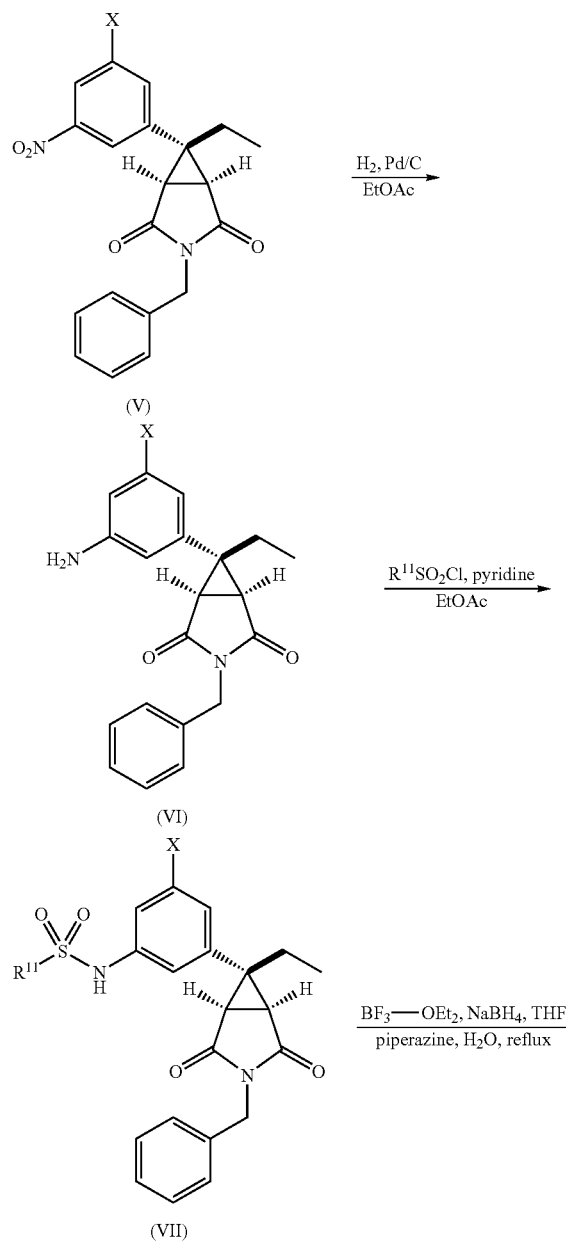

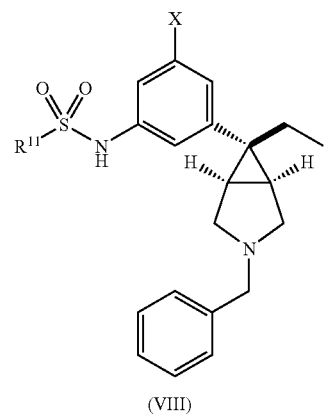

(VIII)

Alternatively, compounds of formula (VIII) can also be prepared according to the chemistry described in Scheme III. Referring to Scheme III below, compounds of formula (X) can be prepared by treatment of a compound of formula (IX) with a reducing agent, such as sodium borohydride, in the presence of boron trifluoride diethyl etherate. This reaction is carried out in solvents such as ethyl ether or tetrahydrofuran, at temperatures ranging from room temperature, to about the reflux temperature, preferably at about the reflux temperature. Treatment of a compound of formula (X) with benzophenone imine, a suitable catalyst such as palladium (II) acetate and BINAP, and a base, such as sodium tert-butoxide, in toluene, at temperatures ranging from room temperature to about the reflux temperature, produces the desired compound of formula (XI). Treatment of an aniline of formula (XI) with an appropriately substituted sulfonyl chloride, such as methanesulfonyl chloride, in the presence of a suitable base, such as pyridine or triethyl amine, in a solvent such as ethyl acetate, at temperatures ranging from 0° C. to room temperature, preferably at about room temperature, produces the desired sulfonamide of formula (VIII).

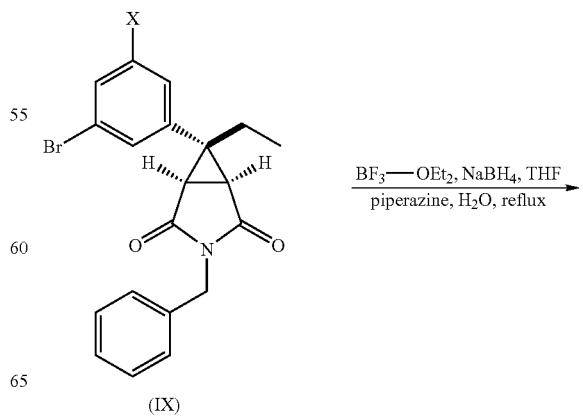

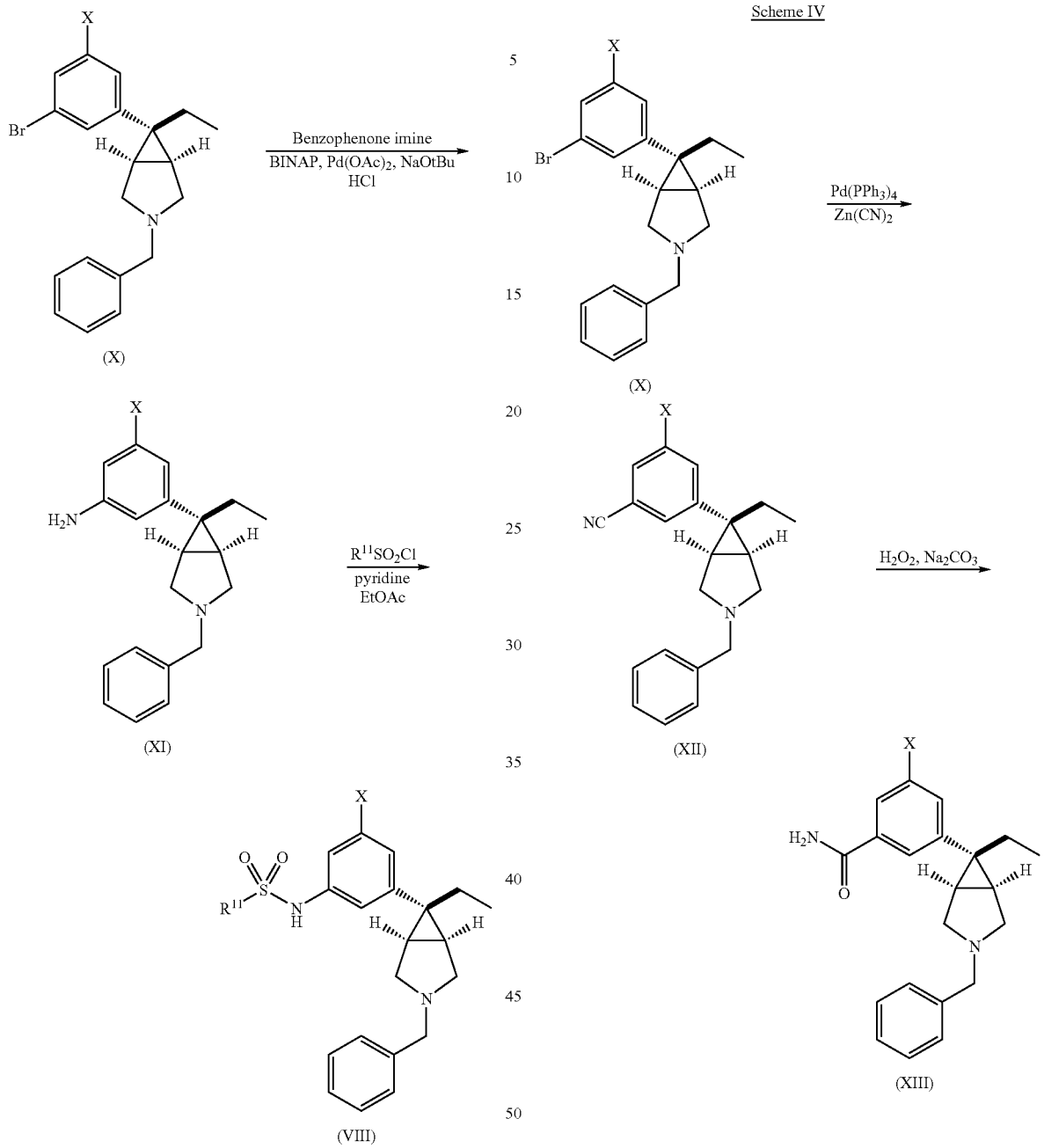

Referring to Scheme IV below, treatment of a bromide of formula (X) with zinc cyanide, in the presence of a suitable catalyst, such as tetrakistriphenylphosphine palladium (0), in solvents such as dimethylformamide, at temperatures ranging from room temperature to about the reflux temperature, preferably at about 85° C., produces the corresponding nitrile of formula (XII). Oxidation of a nitrile of formula (XII) with dilute hydrogen peroxide, in the presence of a suitable alkali metal base, such as sodium carbonate, in solvents such as dimethylformamide or dimethylsulfoxide, at temperatures ranging from 0° C. to about room temperature, preferably at about room temperature, produces the corresponding amide of formula (XIII).

reducing agent, such as sodium borohydride, in the presence of boron trifluoride diethyl etherate, in solvents such as ethyl ether or tetrahydrofuran, at temperatures ranging from room temperature, to about the reflux temperature, preferably at about the reflux temperature, produces the desired compound of formula (XV). Treatment of a compound of formula (XV) with boron trichloride, in the presence of a tetra-alkylammonium salt, such as tetrabutylammonium iodide, in solvents such as dichloromethane or dichloroethane, at temperatures ranging from −78° C. to about room temperature, preferably at about room temperature, produces the corresponding phenol of formula (XVI). Alternative reaction conditions for the above mentioned transformation can also include treatment with aqueous hydrobromic acid and acetic acid at about the reflux temperature.

Scheme V

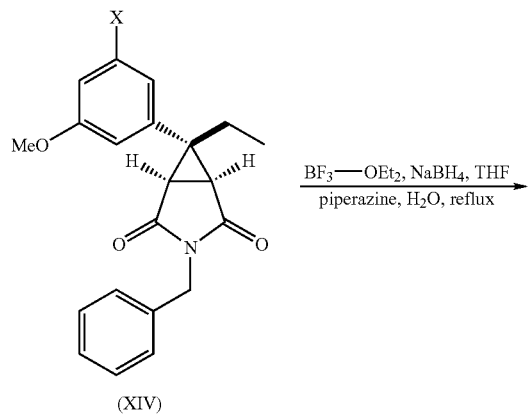

(XIV)

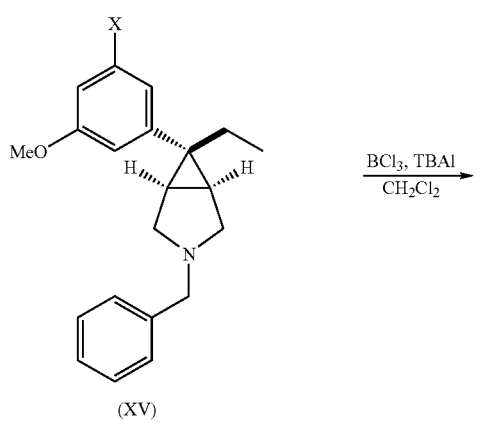

(XV)

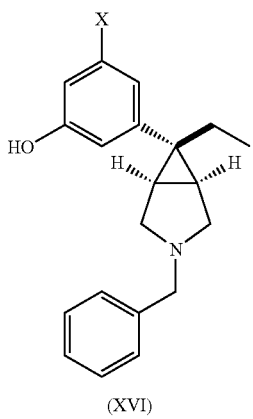

(XVI)

As shown below in Scheme VI, compounds of formula (XVIII) can be prepared by treatment of compounds of formula (XVII) with ammonium formate in the presence of a suitable catalyst, such as palladium on carbon, in alcoholic solvents such as methanol or ethanol, at temperatures ranging from room temperature to about the reflux temperature, preferably at about the reflux temperature. Alternatively, treatment of a compound of formula (XVII) with hydrogen gas (at pressures ranging from atmospheric to 50 psi) in the presence of a suitable catalyst such as palladium on carbon, in alcoholic solvents such as methanol, at temperatures ranging from room temperature to 60° C., preferably at about 60° C., also produces the compound of formula (XVIII).

Scheme VI

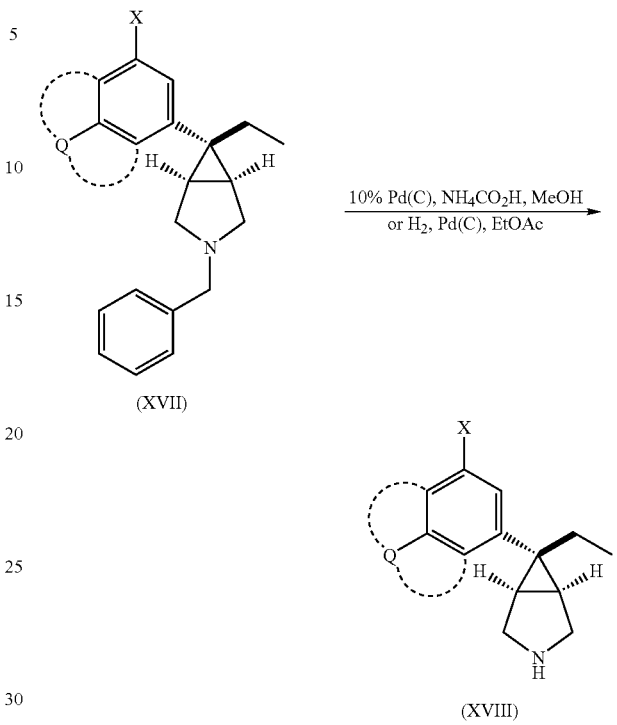

Referring to Scheme VII, treatment of a compound of formula (XVIII) with an appropriately substituted aldehyde of formula (XIX) and a reducing agent such as sodium triacetoxyborohydride, in the presence of acetic acid, in solvents such as dichloromethane or dichloroethane, at temperatures ranging from 0° C. to about room temperature, preferably at about room temperature, produce the corresponding compounds of formula (XXII). Alternatively, compounds of formula (XXII) can also be prepared by treatment of a compound of formula (XVIII) with a suitable alkylating reagent of formula (XX). This reaction should be carried out in the presence of a suitable base, such as potassium carbonate, in solvents such as acetonitrile, at temperatures ranging from room temperature to about the reflux temperature, preferably at about the reflux temperature, which produces the desired compounds of formula (XXII). Reagents XIX and XX can be prepared using methods that are known to one of ordinary skill in the art.

Scheme VII

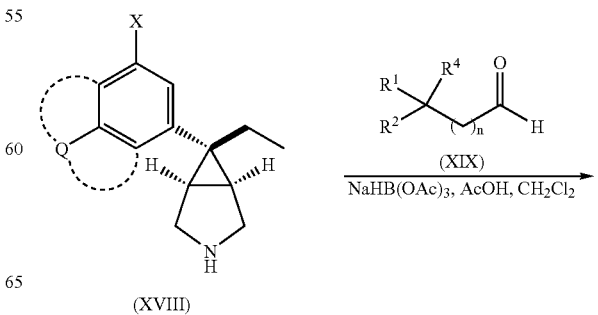

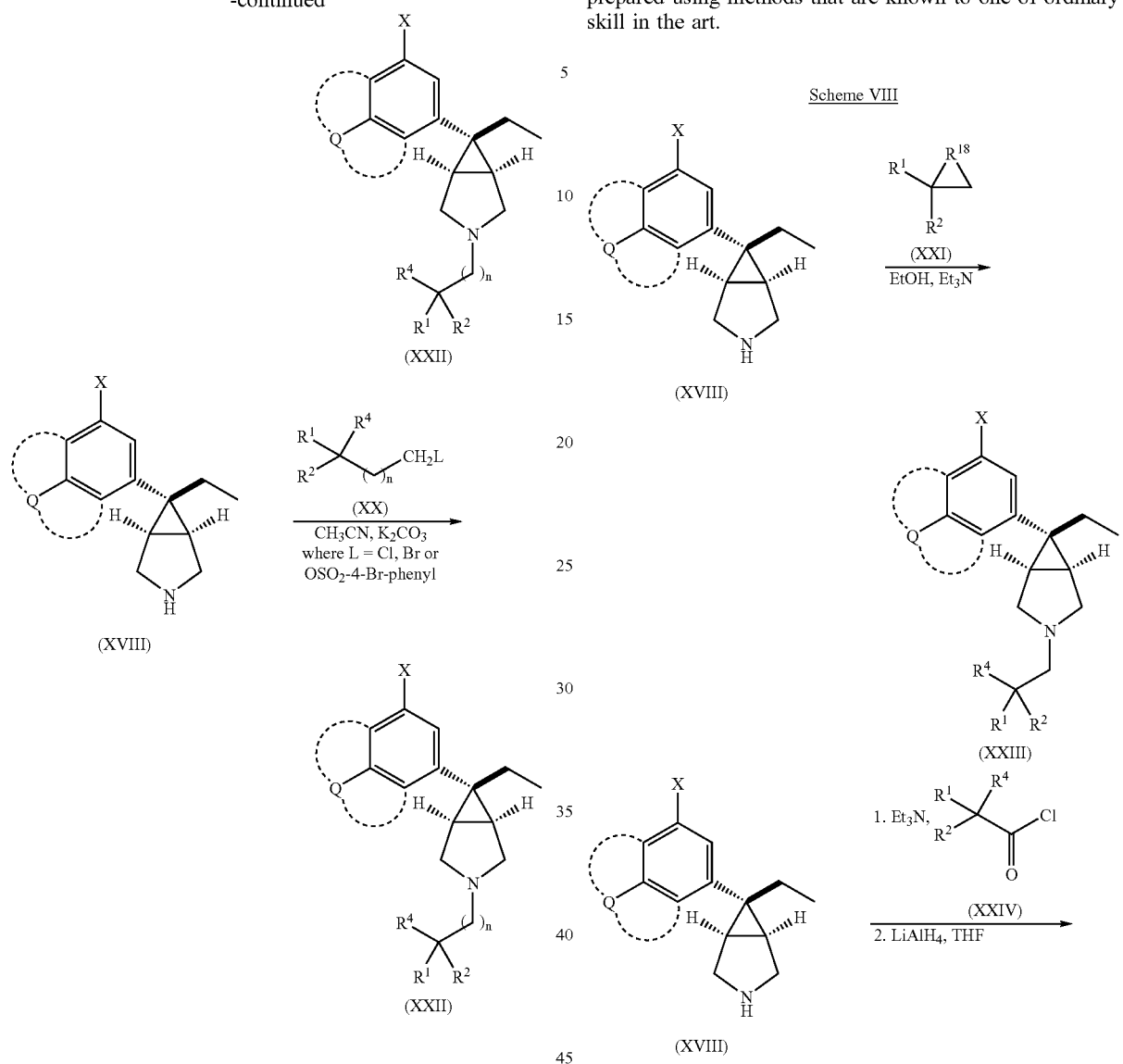

Referring to Scheme VIII below, compounds of formula (XXIII) can be prepared by treatment of a compound of formula (XVIII) with a reagent of formula (XXI) wherein $R^{18}$ is oxygen or —NH—. This reaction should be carried out in the presence of a suitable base such as triethyl amine, in alcoholic solvents such as ethanol, at temperatures ranging from room temperature to about the reflux temperature, preferably at about the reflux temperature to produce the desired compound of formula (XXIII). Alternatively, compounds of formula (XXII) can further be prepared by treatment of a compound of formula (XVIII) with an appropriately substituted acid chloride of formula (XXIV). The reaction should be carried out in the presence of a suitable base such as $Et_3N$ or pyridine, in solvents such as tetrahydrofuran or methylene chloride, at temperature ranging from 0° C. to room temperature, preferably at about room temperature. The amide products from this reaction (not depicted) are then reduced with a suitable reducing agent such as lithium aluminum hydride, in solvents such as ethyl ether or tetrahydrofuran, at temperatures ranging from room temperature to about the reflux temperature, preferably at about the reflux temperature, which produce the desired products of formula (XXII). Reagents XXI and XXIV can be prepared using methods that are known to one of ordinary skill in the art.

Further compounds of formula I, as described herein, can be prepared by transformations using methods that are well known in the art.

The stereochemistry of compounds of formula I synthesized according to the methods described above can be determined using standard spectroscopic methods. Isolation of the exo diastereomer of a compound of formula I from an exo/endo mixture can be accomplished using standard separation methods know to those of ordinary skill in the art, for example crystallization or chromatographic methods.

Pharmaceutically acceptable salts of a compound of formula I can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously), rectally, topically, or by inhalation. In general, the daily dosage for treating a disorder or condition as described herein using a compound of formula I will be about from about 0.01 to about 100 mg per kg, preferably from about 0.1 to about 10 mg per kg, of the body weight of the animal to be treated. As an example, a compound of the formula I, or a pharmaceutically acceptable salt thereof, can be administered for treatment to an adult human of average weight (about 70 kg) in a dose ranging from about 0.5 mg up to about 10 g per day, preferably from about 10 mg to about 1 g per day, in single or divided (i.e., multiple) portions. Variations based on the aforementioned dosage ranges may be made by a physician of ordinary skill taking into account known considerations such as the weight, age, and condition of the animal being treated, the severity of the affliction, and the particular route of administration chosen.

Compounds of formula I of the present invention have been found to display activity in opioid receptor binding assays selective for the mu, kappa and delta opioid receptors. Assays for mu, kappa and delta opioid receptor binding can be performed according to the following procedure:

Affinity of a compound for the delta opioid receptor can be assessed using binding of the delta opioid receptor ligand [$^3$H]-naltrindole to NG108-15 neuroblastoma-glioma cells according to modification of the protocol described in Law et al. (Law, P. Y., Koehler, J. E. and Loh, H. H., "Comparison of Opiate Inhibition of Adenylate Cyclase Activity in Neuroblastoma N18TG2 and Neuroblastoma X Glioma NG108-15 Hybrid Cell Lines", *Molecular Pharmacology*, 21: 483–491 (1982)). Law et al. is incorporated herein in its entirety by reference. Affinity of a compound for the kappa opioid receptor can be assessed using binding of [$^3$H]-bremazocine to kappa receptors as described in Robson, L. E., et al., "Opioid Binding Sites of the Kappa-type in Guinea-pig Cerebellum", *Neuroscience (Oxford)*, 12(2): 621–627 (1984). Robson et al. is incorporated herein it its entirey by reference. For assessment of a compound for mu opioid receptor activity, the mu receptor ligand [$^3$H]-DAMGO (Perkin Elmer Life Sciences, Boston, Mass.; specific activity 55 Ci/mmol, 1.5 nM) is used with rat forebrain tissue. Briefly, the binding is initiated with the addition of a crude membrane preparation of rat forebrain tissue to 96-well polypropylene plates containing the radioligand [$^3$H]-DAMGO and test compound, and are incubated for about 90 minutes at about 25° C. The assay is terminated by rapid filtration with 50 mM Tris HCl pH 7.4 onto Wallac Filtermat B and counted on a Betaplate reader (Wallac).

The data generated can be analyzed using IC$_{50}$ analysis software in Graphpad Prism. Ki values can be calculated using Graphpad Prism according to the following formula:

$$Ki = IC_{50}/1 + [^3H \text{ ligand}]/K_D$$

where IC$_{50}$ is the concentration at which 50% of the $^3$H ligand is displaced by the test compound and K$_D$ is the dissociation constant for the $^3$H ligand at the receptor site.

Biological Activity

The Ki values of the specific compounds of formula I of Examples 7, 8, and 9, infra, in a mu opioid receptor binding assay to brain tissue such as that described above were determined. These compounds were all found to have Ki values of about 200 nM or less for the mu receptor.

The compounds of formula I are biologically advantageous in that they are not metabolized by the p450 isozyme CYP2D6. Since variability in the presence of CYP2D6 in the human population exists, it is beneficial to have a medicine that is not metabolized by CYP2D6 because effective dosages across the human population will be independent of CYP2D6 differences.

Whether a compound is metabolized by CYP2D6 can be determined using CYP2D6, for example that purchased from PanVera Corporation (Madison, Wis.). Identification of compounds that are subsrates of CYP2D can be determined, for example, according to the following assay.

Compounds are incubated with human recombinant CYP2D6 BACULOSOMES™ (PanVera Corporation; Madison, Wis.). More particularly, compound (1 uM), rCYP2D6 (2.8 pmol/ml), buffer(100 mM phosphate, pH=7.4) and NADPH (1.67 mg/ml, Sigma Aldrich #201–210) are incubated at 37° C. Aliquots (50 ul) are taken at 0, 5, 10, 20 and 30 minutes, and the reaction is quenched by addition of ice cold sodium carbonate buffer (50 ul, 20 mM pH=10.5, with internal standard). The resulting solution is extracted (10×volume of tert-butyl methyl ester) and samples were analyzed by LC/MS. Loss of parent compound is monitored, and half-life for parent compound disappearance is calculated using WinNonlin.

The following Examples illustrate the present invention. It is to be understood, however, that the invention, as fully described herein and as recited in the claims, is not intended to be limited by the details of the following Examples.

EXAMPLES

Preparation 1

1-(3,5-Difluoro-phenyl)-propylidene-hydrazine

To a stirring solution of 1-(3,5-Difluoro-phenyl)-propan-1-one (5.00 g, 29.40 mmol) in 5.0 mL of $CH_3OH$ was added a solution of hydrazone (35% in $H_2O$, 42.00 mL, 29.40 mmol). The mixture was then heated to 75° C. for 1 h, cooled to ambient temperature, and poured into equal amounts of $CH_2Cl_2$ and $H_2O$. The organic layer was then collected and washed with a saturated solution of NaCl. The organic layer was then dried over $MgSO_4$, and concentrated under reduced pressure to yield an 8:1 mixture of hydrazone isomers (5.53 g, >95%) as yellow oil. (Major isomer) 400 MHz $^1$H NMR ($CDCl_3$) δ 7.11–7.16 (m, 2H), 6.65–6.71 (m, 1H), 5.52 (br s, 2H), 2.53 (q, J=7.88, 2H), 1.18 (t, J=7.05, 3H).

The following compounds were made using the procedure of Preparation 1.

1-(3-Bromo-5-fluoro-phenyl)-propylidene-hydrazine

400 MHz $^1$H NMR ($CDCl_3$) δ 7.54–7.55 (m, 1H), 7.24–7.29 (m, 1H), 7.19–7.22 (m, 1H), 5.52 (s, 2H), 2.54 (q, J=7.88, 2H), 1.12 (t, 3H).

1-(3-Methoxy-phenyl)-propylidene-hydrazine

400 MHz $^1$H NMR ($CDCl_3$) δ 7.15–7.24 (m, 3H), 6.80–6.83 (m, 1H), 5.41 (br s, 2H), 3.78 (s, 3H), 2.57 (q, J=7.88, 2H), 1.12 (t, 3H).

1-(3-Nitro-phenyl)-propylidene-hydrazine

400 MHz $^1$H NMR ($CD_3OD$) δ 8.48 (s, 1H), 8.14 (d, 1H), 7.99 (d, 1H), 7.55 (t, 1H), 2.68 (q, 2H), 1.17 (t, 3H).

1-(3-Bromo-phenyl)-propylidene-hydrazine

400 MHz $^1$H NMR ($CDCl_3$) δ 7.77 (s, 1H), 7.45–7.66 (m, 1H), 7.22–7.30 (m, 1H), 7.16 (t, 1H), 5.45 (brs, 2H), 2.51 (q, 2H), 1.10 (t, 3H); MS (M+1) 227.1.

1-(3,5-Dibromo-phenyl)-propylidene-hydrazine

400 MHz $^1$H NMR ($CDCl_3$) δ 7.96 (s, 1H), 7.68 (s, 1H), 7.53 (s, 1H), 5.52 (brs, 2H), 2.53 (q, 2H), 1.12 (t, 3H).

1-(3-Bromo-phenyl)-butylidene-hydrazine

400 MHz $^1$H NMR ($CDCl_3$) δ 7.75 (s, 1H), 7.45–7.47 (m, 1H), 7.32–7.33 (m, 1H), 7.09–7.14 (m, 1H), 5.47 (brs, 2H), 2.44–2.48 (m, 2H), 1.45–1.49 (m, 2H), 0.91–0.94 (m, 3H).

1-(3-Bromo-phenyl)-2-methyl-propylidene-hydrazine

400 MHz $^1$H NMR ($CDCl_3$) δ 7.46–7.50 (m, 1H), 7.25–7.31 (m, 2H), 7.07–7.09 (m, 1H), 4.92 (brs, 2H), 2.61–2.68 (m, 1H), 1.03 (d, J=6.6 Hz, 6H); MS (M+1) 241.1.

Preparation 2

Exo-3-Benzyl-6-(3,5-difluoro-phenyl)-6-ethyl-3-aza-bicyclo[3.1.0]hexane-2,4-dione To a stirring solution of 1-(3,5-Difluoro-phenyl)-propylidene-hydrazine (prepared as described in Preparation 1, 5.40 g, 29.40 mmol) in 60.0 mL of dioxane at room temperature was added $MnO_2$. The mixture stirred for 45 min., at which point the black suspension that had formed was filtered off over a pad of celite, which was then washed with 20.0 mL of dioxane. The resulting deep red solution was then treated with 1-Benzyl-pyrrole-2,5-dione in portions over a 20 min. period. The mixture stirred at room temperature for 1.75 h. It was then heated to 100° C. for 21 h., cooled to room temperature, and was concentrated under reduced pressure. The light yellow oil was then treated with warm $CH_3OH$ and a white solid was filtered off. The solid was recrystallized from $CH_3OH$ to yield the desired product (6.46 g, 64%) as a white solid. 400 MHz $^1$H NMR ($CDCl_3$) δ 7.37–7.40 (m, 2H), 7.22–7.30 (m, 3H), 6.77–6.82 (m, 2H), 6.67–6.72 (m, 1H), 4.58 (s, 2H), 2.69 (s, 2H), 1.39 (q, J=7.47, 2H), 0.67 (t, J=7.47 3H).

The following compounds were made using the procedure in Preparation 2.

Exo-3-Benzyl-6-(3-bromo-5-fluoro-phenyl)-6-ethyl-3-aza-bicyclo[3.1.0]hexane-2,4-dione 400 MHz $^1$H NMR ($CDCl_3$) δ 7.37–7.40 (m, 2H), 7.25–7.31 (m, 4H), 7.12–7.15 (m, 1H), 6.91–6.95 (m, 1H), 4.58 (s, 2H), 2.69 (s, 2H), 1.39 (q, 7.47, 2H), 0.67 (t, J=7.47, 3H).

Exo-3-Benzyl-6-ethyl-6-(3-methoxy-phenyl)-3-aza-bicyclo[3.1.0]hexane-2,4-dione

400 MHz $^1$H NMR ($CDCl_3$) δ 7.38–7.41 (m, 2H), 7.17–7.30 (m, 4H), 6.83–6.85 (m, 1H), 6.75–6.79 (m, 2H), 4.58 (s, 2H), 3.76 (s, 3H), 2.72 (s, 2H), 1.41 (q, J=7.47, 2H), 0.67 (t, J=7.47).

Exo-3-Benzyl-6-(3-bromo-phenyl)-6-ethyl-3-aza-bicyclo[3.1.0]hexane-2,4-dione

400 MHz $^1$H NMR ($CDCl_3$) δ 7.36–7.43 (m, 4H), 7.15–7.30 (m, 5H), 4.58 (s, 2H), 2.70 (s, 2H), 1.40 (q, J=7.47, 2H), 0.66 (t, J=7.47, 3H).

Exo-3-Benzyl-6-ethyl-6-(3-nitro-phenyl)-3-aza-bicyclo[3.1.0]hexane-2,4-dione

400 MHz $^1$H NMR ($CD_3OD$) δ 8.18–8.21 (m, 2H), 7.77–7.79 (m, 1H), 7.61 (t, 1H), 7.38–7.41 (m, 2H), 7.23–7.33 (m, 3H), 4.62 (s, 2H), 2.95 (s, 2H), 1.46 (q, 2H), 0.67 (t, 3H).

Exo-3-Benzyl-6-(3,5-dibromo-phenyl)-6-ethyl-3-aza-bicyclo[3.1.0]hexane-2,4-dione 400 MHz $^1$H NMR (CDCl$_3$) δ 7.55 (s, 1H), 7.25–7.40 (m, 7H), 4.58 (s, 2H), 2.68 (s, 2H), 1.37 (q, 2H), 0.66 (t, J=7.47, 3H).

Exo-3-Benzyl-6-(3-bromo-phenyl)-6-propyl-3-aza-bicyclo[3.1.0]hexane-2,4-dione 400 MHz $^1$H NMR (CD$_3$OD) δ 7.46–7.47 (m, 1H), 7.36–7.41 (m, 3H), 7.20–7.30 (m, 5H), 4.57 (s, 2H), 2.82 (s, 2H), 1.29–1.33 (m, 2H), 0.99–1.07 (m, 2H), 0.42 (t, J=7.5 Hz, 3H).

Exo-3-Benzyl-6-(3-bromo-phenyl)-6-isopropyl-3-aza-bicyclo[3.1.0]hexane-2,4-dione 400 MHz $^1$H NMR (CDCl$_3$) δ 7.37–7.40 (m, 4H), 7.21–7.30 (m, 3H), 7.12–7.18 (m, 2H), 4.58 (s, 2H), 2.69 (s, 2H), 1.18–1.25 (m, 1H), 0.67 (d, J =6.6 Hz, 6H); MS (M+1) 400.0.

Preparation 3

Exo-6-(3-Amino-phenyl)-3-benzyl-6-ethyl-3-aza-bicyclo[3.1.0]hexane-2,4-dione A solution of Exo-3-Benzyl-6-ethyl-6-(3-nitro-phenyl)-3-aza-bicyclo[3.1.0]hexane-2,4-dione (prepared as described in Preparation 2, 15.2 g, 43.4 mmol) in 150 mL ethyl acetate was treated with 30 psi H$_2$ and 10% Pd (C) (750 mg) for 6 hours at room temperature. The mixture was filtered through a celite pad and concentrated to yield 14 g of the desired product. 400 MHz $^1$H NMR (CD$_3$OD) δ 7.38–7.40 (m, 2H), 7.23–7.35 (m, 3H), 7.14 (t, 1H), 6.67 (s, 1H), 6.58–6.61 (m, 2H), 4.60 (s, 2H), 2.79 (s, 2H), 1.36–1.42 (m, 2H), 0.65–0.71 (m, 3H); MS (M+1) 362.2.

Exo-N-[3-(3-Benzyl-6-ethyl-2,4-dioxo-3-aza-bicyclo[3.1.0]hex-6-yl)-phenyl]-methanesulfonamide To a stirring solution of Exo-6-(3-Amino-phenyl)-3-benzyl-6-ethyl-3-aza-bicyclo[3.1.0]hexane-2,4-dione (prepared as described above, 25 g, 78.1 mmol) in ethyl acetate was added methanesulfonyl chloride (6.35 mL, 82.2 mmol) and triethyl amine (13.1 mL, 93.8 mmol). The solution warmed to room temperature and stirred for 16 hours. The solid ppt formed was filtered off and the remaining solution was treated with 1N HCl, brine and water. The organic layer was dried with MgSO$_4$, filtered and concentrated. The remaining crude material was triturated with Et$_2$O to yield 30 g of the desired product. 400 MHz $^1$H NMR (CDCl$_3$) δ 7.40–7.46 (m, 2H), 7.22–7.37 (m, 5H), 7.11–7.20 (m, 2H), 4.60 (s, 2H), 3.05 (s, 3H), 2.77 (s, 2H), 1.38–1.42 (m, 2H), 0.65–0.71 (m, 3H); MS (M+1) 399.2.

Example 1

Exo-N-[3-(3-Benzyl-6-ethyl-3-aza-bicyclo[3.1.0]hex-6-yl)-phenyl]-methanesulfonamide To a cooled slurry of Exo-N-[3-(3-Benzyl-6-ethyl-2,4-dioxo-3-aza-bicyclo[3.1.0]hex-6-yl)-phenyl]-methanesulfonamide (prepared as described above, 30 g, 75.4 mmol) in THF at −5° C. was added sodium borohydride (6.0 g, 158.3 mmol), followed by the slow addition of boron trifluoride diethyl etherate (26.8 mL, 211.1 mmol). The mixture was allowed to warm to room temperature and stirred for 2 h. It was then heated to reflux for 16 hours. The mixture was then cooled to 0° C. and piperazine (30 g) was carefully added dropwise in 300 mL of H$_2$O. The mixture was stirred at room temperature 2 hours and diluted with Et$_2$O. The layers were separated, the aqueous layer was extracted with Et2O and the combined organic layers were dried and concentrated. Purification yielded 19.2 g of desired product. 400 MHz $^1$H NMR (CD$_3$OD) δ 7.28–7.33 (m, 4H), 7.19–7.23 (m, 2H), 7.15 (s, 1H), 7.05–7.11 (m, 2H), 3.64 (s, 2H), 2.91–2.97 (m, 2H), 2.90 (s, 3H), 2.82–2.88 (m, 2H), 1.96–2.05 (m, 2H), 1.79–1.82 (m, 2H), 0.83 (t, 3H).

Example 2

Exo-3-Benzyl-6-(3,5-difluoro-phenyl)-6-ethyl-3-aza-bicyclo[3.1.0]hexane

In flame-dried glassware under N$_2$, Exo-3-Benzyl-6-(3,5-difluoro-phenyl)-6-ethyl-3-aza-bicyclo[3.1.0]hexane-2,4-dione (prepared as described in Preparation 2, 2.95 g, 8.64 mmol) and sodium borohydride (689 mg, 18.15 mmol) were combined in 100 mL of anhydrous THF. The mixture was cooled to −5° C. and borontrifluoride diethylethrate (2.67 mL, 24.19 mmol) was added dropwise. The mixture was allowed to warm to room temperature and stirred for 2 h. It was then heated to reflux for 3 h. The mixture was then cooled to 0° C. and piperazine (4.46 g, 51.85 mmol) was carefully added dropwise in 30 mL of H$_2$O. The reaction was then heated to reflux for 18 h. The mixture was then allowed to cool to room temperature, upon which it was diluted with H$_2$O and extracted twice with ethyl acetate. The combined extracts were washed twice with H$_2$O, washed once with a saturated solution of NaCl, and dried over MgSO$_4$. The liquid was then concentrated under reduced pressure to yield the desired product (2.62 g, 97%) as a clear, colorless oil. 400 MHz $^1$H NMR (CDCl$_3$) δ 7.27–7.32 (m, 5H), 6.70–6.76 (m, 2H), 6.55–6.60 (m, 1H), 3.65 (br s, 2H), 3.03 (d, 2H), 2.79 (br s, 2H), 2.00–2.07 (m, 2H), 1.74 (s, 2H), 0.83 (t, 3H).

The following compounds were made according to the procedure in Example 2.

Exo-3-Benzyl-6-(3-bromo-5-fluoro-phenyl)-6-ethyl-3-aza-bicyclo[3.1.0]hexane

400 MHz $^1$H NMR (CDCl$_3$) δ 7.23–7.32 (M, 4H), 7.15–7.22 (m, 2H), 6.96–7.03 (m, 1H), 6.85–6.88 (m, 1H), 3.64 (s, 2H), 3.04 (d, J=10.0, 2H), 2.76–2.78 (m, 2H), 2.02–2.08 (m, 2H), 1.73 (d, J=1.6, 2H), 0.83 (t, 3H).

Exo-3-Benzyl-6-(3-bromo-phenyl)-6-ethyl-3-aza-bicyclo[3.1.0]hexane

400 MHz $^1$H NMR (CDCl$_3$) δ 7.39–7.40 (m, 1H), 7.21–7.34 (m, 6H), 7.09–7.18 (m, 2H), 3.66 (s, 2H), 3.05 (d, J=9.54, 2H), 2.77–2.81 (m, 2H), 2.04–2.10 (m, 2H), 1.73–1.78 (m, 2H), 0.85 (t, J=7.47, 3H).

Exo-3-Benzyl-6-(3,5-dibromo-phenyl)-6-ethyl-3-aza-bicyclo[3.1.0]hexane

400 MHz $^1$H NMR (CDCl$_3$) δ 7.43 (s, 1H), 7.21–7.32 (m, 7H), 3.63 (s, 2H), 3.03 (d, J=9.54, 2H), 2.73–2.76 (m, 2H), 2.02–2.08 (m, 2H), 1.70–1.74 (m, 2H), 0.82 (t, J=7.47, 3H); MS (M+1) 436.0.

Exo-3-Benzyl-6-ethyl-6-(3-methoxy-phenyl)-3-aza-bicyclo[3.1.0]hexane

400 MHz $^1$H NMR (CDCl$_3$) δ 7.22–7.35 (m, 5H), 7.17–7.21 (m, 1H), 6.82–6.88 (m, 2H), 6.71–6.74 (m, 1H), 3.79 (s, 3H), 3.68 (s, 2H), 3.06 (d, J=9.54, 2H), 2.81–2.84 (m, 2H), 2.08 (q, 2H), 1.80–1.82 (m, 2H), 0.88–0.91 (m, 3H); MS (M+1) 308.2

Exo-3-Benzyl-6-(3-bromo-phenyl)-6-propyl-3-aza-bicyclo[3.1.0]hexane; 400 MHz $^1$H NMR (CDCl$_3$) δ 7.38–7.39 (m, 1H), 7.07–7.33 (m, 8H), 3.65 (s, 2H), 3.05 (d, J=9.5 Hz, 2H), 2.75–2.78 (m, 2H), 2.00–2.27 (m, 2H), 1.70–1.75 (m, 2H), 1.17–1.27 (m, 2H), 0.88 (t, J=7.5 Hz, 3H).

Exo-3-Benzyl-6-(3-bromo-phenyl)-6-isopropyl-3-aza-bicyclo[3.1.0]hexane; 400 MHz $^1$H NMR (CDCl$_3$) δ 7.19–7.41 (m, 7H), 7.06–7.14 (m, 2H), 3.65 (s, 2H), 3.00 (d, J=9.5 Hz, 2H), 2.83–2.86 (m, 2H), 2.58–2.61 (m, 1H), 1.76–1.78 (m, 2H), 0.83 (d, J=6.6 Hz, 6H).

Example 3

Exo-2-Methoxy-ethanesulfonic acid [3-(3-benzyl-6-ethyl-3-aza-bicyclo[3.1.0]hex-6-yl)-phenyl]-amide To a stirring solution of Exo-3-Benzyl-6-(3-bromo-phenyl)-6-ethyl-3-aza-bicyclo[3.1.0]hexane (prepared as described in Example 2, 3.2 g, 8.98 mmol) in 25 mL anhydrous toluene at room temperature was added benzophenone imine (1.81 mL, 10.8 mmol), BINAP (8 mg, 0.013 mmol), palladium (II) acetate (2.0 mg, 0.009 mmol) and sodium tert-butoxide (1.2 g, 12.57 mmol). The mixture was cooled to −78° C. and de-oxygenated with vacuum/N$_2$ purge. The mixture was heated at mild reflux for 16 hours and cooled to room temperature. The mixture was then treated with 7 mL of concentrated HCl and 30 mL of water and was heated at reflux for 4 hours. The mixture was cooled to 0° C. and the pH was adjusted to 12 with 1N NaOH. The layers were separated, the aqueous layer was extracted with CH$_2$Cl$_2$ (3×30 mL) and the combined organic layers were dried and concentrated to yield 1.87 gm of product. The crude aniline was used in the next step without purification.

To a stirring solution of the aniline (1.0 g, 3.42 mmol) prepared above in 10 mL anhydrous pyridine at 0° C. was added 2-Methoxy-ethanesulfonyl chloride (814 mg, 5.13 mmol). The reaction was warmed to room temperature and stirred for 3 hours. Cold saturated NaHCO$_3$ was added and the mixture was diluted with ethyl acetate. The layers were separated, the aqueous layer extracted with ethyl acetate and the combined organic layers were dried over MgSO$_4$ and concentrated. The crude material was purified by flash chromatography with 70% ethyl acetate/hexanes to yield 1.1 gm of pure product. 400 MHz $^1$H NMR (CDCl$_3$) δ 7.23–7.30 (m, 5H), 7.13–7.20 (m, 2H), 7.01–7.08 (m, 2H), 3.78 (t, J=5.6 Hz, 2H), 3.64 (s, 2H), 3.36 (s, 3H), 3.21 (t, J=5.6 Hz, 2H), 3.19 (d, J=9.9 Hz, 2H), 2.76–2.79 (m, 2H), 2.02–2.07 (m, 2H), 1.73–1.75 (m, 2H), 0.83 (t, 3H); MS (M+1) 415.1.

The following compounds were made according to the procedure in Example 3.

Exo-1-Methyl-1H-imidazole-4-sulfonic acid [3-(3-benzyl-6-ethyl-3-aza-bicyclo[3.1.0]hex-6-yl)-phenyl]-amide 400 MHz $^1$H NMR (CDCl$_3$) δ 7.41 (s, 1H), 7.21–7.31 (m, 6H), 6.91–7.11 (m, 4H), 3.67 (bs, 2H), 3.60 (s, 3H), 2.80–2.95 (brm, 4H), 1.91–1.95 (m, 2H), 1.71 (brs, 2H), 0.70 (t, 3H); MS (M+1) 437.0.

Exo-N-[3-(3-Benzyl-6-ethyl-3-aza-bicyclo[3.1.0]hex-6-yl)-5-fluoro-phenyl]-methanesulfonamide 400 MHz $^1$H NMR (CDCl$_3$) δ 7.28–7.34 (M, 5H), 6.80–6.84 (m, 2H), 6.73–6.76 (m, 1H), 3.64 (s, 2H), 3.00–3.04 (m, 5H), 2.76–2.80 (m, 2H), 2.02–2.07 (m, 2H), 1.72–1.74 (m, 2H), 0.83 (t, 3H); MS (M+1) 389.1

Exo-N-[3-(3-Benzyl-6-propyl-3-aza-bicyclo[3.1.0]hex-6-yl)-phenyl]-methanesulfonamide 400 MHz $^1$H NMR (CDCl$_3$) δ 7.28–7.30 (m, 4H), 7.17–7.27 (m, 2H), 7.00–7.08 (m, 3H), 3.64 (s, 2H), 3.02 (d, J=9.5 Hz, 2H), 2.96 (s, 3H), 2.75–2.77 (m, 2H), 1.97–2.02 (m, 2H), 1.71–1.73 (m, 2H), 1.17–1.25 (m, 2H), 0.85 (t, J=7.5 Hz, 3H).

Exo-N-[3-(3-Benzyl-6-isopropyl-3-aza-bicyclo[3.1.0]hex-6-yl)-phenyl]-methanesulfonamide 400 MHz $^1$H NMR (CDCl$_3$) δ 7.28–7.31 (m, 4H), 7.16–7.26 (m, 2H), 7.01–7.09 (m, 3H), 3.65 (s, 2H), 2.95–2.99 (m, 5H), 2.84–2.86 (m, 2H), 2.55–2.59 (m, 1H), 1.75–1.77 (m, 2H), 0.82 (d, J=7.1 Hz, 6H).

Exo-N-[3-(3-Benzyl-6-ethyl-3-aza-bicyclo[3.1.0]hex-6-yl)-5-cyano-phenyl]-methanesulfonamide 400 MHz $^1$H NMR (CDCl$_3$) δ 7.20–7.31 (m, 8H), 3.63 (s, 2H), 3.04–3.07 (m, 2H), 3.02 (s, 3H), 2.74–2.78 (m, 2H), 2.08 (q, J=7.5 Hz, 2H), 1.71–1.72 (m, 2H), 0.81 (t, J=7.5 Hz, 3H); MS (M+1) 396.3.

Exo-Ethanesulfonic acid [3-(3-benzyl-6-ethyl-3-aza-bicyclo[3.1.0]hex-6-yl)-phenyl]-amide 400 MHz $^1$H NMR (CDCl$_3$) δ 7.17–7.34 (m, 6H), 6.99–7.07 (m, 3H), 3.66 (s, 2H), 3.01–3.10 (m, 4H), 2.81–2.83 (m, 2H), 2.01 (q, J=7.5 Hz, 2H), 1.82–1.84 (m, 2H), 1.31–1.34 (m, 3H), 0.79–0.83 (m, 3H); MS (M+1) 385.3.

Example 4

Exo-3-(3-Benzyl-6-ethyl-3-aza-bicyclo[3.1.0]hex-6-yl)-benzamide

To a stirring solution of Exo-3-Benzyl-6-(3-bromo-phenyl)-6-ethyl-3-aza-bicyclo[3.1.0]hexane (prepared as described in Example 2, 5.0 g, 14.0 mmol) in 75 mL anhydrous DMF at room temperature was added zinc cyanide (2.5 g, 21.0 mmol) and tetrakistriphenylphosphine palladium (0) (8.1 g, 7.0 mmol). The mixture was cooled to −78° C. and de-oxygenated with vacuum/N$_2$ purge. The mixture was warmed to room temperature and then heated at 85° C. for 3 hours. The mixture was cooled to room temperature and diluted with ethyl acetate and water. The layers were separated, the aqueous layer extracted with ethyl acetate, the combined organic layers were dried over MgSO$_4$ and filtered through a small silica gel plug. The solution was concentrated to yield the crude nitrile (3.4 g), which was used without purification.

To a stirring solution of the nitrile prepared above (3.4 g, 11.2 mmol) in 90 mL DMSO at room temperature was added 30% H$_2$O$_2$ (5.7 mL, 56 mmol) and potassium carbonate (216 mg, 1.57 mmol). After stirring 3.5 hours, the mixture was diluted with water and extracted with ethyl acetate. The combined organic layers were dried over MgSO₄ and concentrated to yield 3.17 gm of product. 400 MHz ¹H NMR (CDCl₃) δ 7.30–7.39 (m, 5H), 7.09 (t, 1H), 6.70–6.71 (m, 1H), 6.61–6.63 (m, 1H), 6.49–6.51 (m, 1H), 3.70 (s, 2H), 3.56 (brs, 2H), 3.04–3.10 (m, 2H), 2.82–2.87 (m, 2H), 2.04–2.10 (m, 2H), 1.77–1.79 (m, 2H), 0.85–0.89 (m, 3H).

The following compound was made according to the procedure in Example 4.

Exo-3-(3-Benzyl-6-ethyl-3-aza-bicyclo[3.1.0]hex-6-yl)-5-fluoro-benzamide

400 MHz ¹H NMR (CDCl₃) δ 7.47 (s, 1H), 7.21–7.34 (m, 6H), 7.07–7.10 (m, 1H), 6.07 (brs, 1H), 5.90 (brs, 1H), 3.65 (s, 2H), 3.03–3.08 (m, 2H), 2.77–2.80 (m, 2H), 2.05–2.10 (m, 2H), 1.76–1.78 (m, 2H), 0.82 (t, 3H); MS (M+1) 339.2.

Exo-3-(3-Benzyl-6-propyl-3-aza-bicyclo[3.1.0]hex-6-yl)-benzamide

400 MHz ¹H NMR (CDCl₃) δ 7.75–7.77 (m, 1H), 7.57–7.59 (m, 1H), 7.38–7.40 (m, 1H), 7.21–7.33 (m, 6H), 6.59 (brs, 1H), 6.54 (brs, 1H), 3.67 (s, 2H), 3.06 (d, J=9.5 Hz, 2H), 2.80–2.82 (m, 2H), 2.00–2.03 (m, 2H), 1.75–1.80 (m, 2H), 1.18–1.25 (m, 2H), 0.86 (t, J=7.5 Hz, 3H).

Example 5

Exo-3-(3-Benzyl-6-ethyl-3-aza-bicyclo[3.1.0]hex-6-yl)-phenol

To a stirring solution of Exo-3-Benzyl-6-ethyl-6-(3-methoxy-phenyl)-3-aza-bicyclo[3.1.0]hexane (prepared as described in Example 2, 2.63 g, 8.55 mmol) in 42 mL of anhydrous methylene chloride at −78° C. was added TBAI (7.9 g, 21.4 mmol) and a 1M boron trichloride solution (38.5 mL, 38.5 mmol). The reaction was warmed to 0° C. and stirred for 3 hours. Cold aqueous NaHCO₃ was added, the reaction was diluted with methylene chloride and the layers were separated. The aqueous layer was extracted with methylene chloride, the combined organic layers were dried over anhydrous MgSO₄ and concentrated. The crude material was purified by flash chromatography to yield the desired phenol. 400 MHz ¹H NMR (CDCl₃) δ 7.21–7.38 (m, 5H), 7.05 (t, J=7.9 Hz, 1H), 6.73 (d, J=7.5 Hz, 1H), 6.66–6.68 (m, 1H), 6.59–6.61 (m, 1H), 6.00 (brs, 1H), 3.67 (s, 2H), 2.79–2.95 (m, 4H), 1.82–1.88 (m, 2H), 1.77–1.80 (m, 2H), 0.81–0.85 (m, 3H); MS (M+1) 294.5.

Example 6

Exo-6-(3,5-Difluoro-phenyl)-6-ethyl-3-aza-bicyclo[3.1.0]hexane

To a stirring solution of Exo-3-Benzyl-6-(3,5-difluoro-phenyl)-6-ethyl-3-aza-bicyclo[3.1.0]hexane (prepared as described in Example 2, 459 mg, 1.465 mmol) and amonium formate (277 mg, 4.395 mmol) in 14.0 mL of CH₃OH was added palladium on carbon (10% Pd, 184 mg). The mixture was then heated to reflux for 4 h., cooled to room temperature and filtered through a pad of celite, washing with CH₃OH. The filtrate was then concentrated under reduced pressure to yield oily white solids (343 mg). The solids were then dissolved in CH₂Cl₂, basified with 1M NaOH (aq), and neutralized with HCl (aq) and NaHCO₃ (aq). The aqueous layer was then extracted three times with CH₂Cl₂. The combined extracts were dried over MgSO₄ and concentrated under reduced pressure to yield the desired product (105 mg, 32%) as a clear, colorless oil. 400 MHz ¹H NMR (CD₃OD) δ 6.83–6.90 (m, 2H), 6.68–6.77 (m, 1H), 3.46–3.58 (m, 3H), 3.19 (d, J=12.4, 1H), 2.10–2.17 (m, 1H), 1.86–1.87 (m, 1H), 1.60–1.67 (m, 2H), 0.78–0.85 (m, 3H).

Alternative reaction conditions for this process are described as per the example below.

Exo-3-(6-Ethyl-3-aza-bicyclo[3.1.0]hex-6-yl)-5-fluoro-benzamide

In a 500 mL Parr bottle, Exo-3-(3-Benzyl-6-ethyl-3-aza-bicyclo[3.1.0]hex-6-yl)-5-fluoro-benzamide (prepared as described in example 7, 1.40 g, 4.14 mmol) was dissolved in 60 mL methanol at room temperature. To this solution was added 350 mg of 10% Pd(C). The mixture was hydrogenated under 50 psi H₂ at 60° C. for 18 hours. The mixture was cooled to room temperature and filtered through a plug of celite and the pad was washed several times with methanol. The resulting solution was concentrated under reduced pressure to yield 1.3 gm of desired product. 400 MHz ¹H NMR (CD₃OD) δ 7.63 (s, 1H), 7.46 (d, J=8.7 Hz, 1H), 7.25 (d, J=8.7 Hz, 1H), 3.78–3.82 (m, 2H), 3.23–3.31 (m, 2H), 2.33 (brs, 2H), 1.63–1.69 (m, 2H), 0.85 (t, 3H); MS (M+1) 249.1.

The following compounds were made according to the two procedures in Example 6.

Exo-N-[3-(6-Ethyl-3-aza-bicyclo[3.1.0]hex-6-yl)-5-fluoro-phenyl]-methanesulfonamide 400 MHz ¹H NMR (CD₃OD) δ 6.89 (s, 1H), 6.79–6.81 (m, 1H), 6.69–6.72 (m, 1H), 3.21–3.28 (m, 2H), 3.05–3.08 (m, 2H), 2.92 (s, 3H), 1.92–1.94 (m, 2H), 1.61–1.67 (m, 2H), 0.83 (t, 3H); MS (M+1) 299.1.

Exo-3-(6-Ethyl-3-aza-bicyclo[3.1.0]hex-6-yl)-phenol

400 MHz ¹H NMR (CD₃OD) δ 7.05 (t, J=7.5Hz, 1H), 6.66–6.70 (m, 2H), 6.57–6.59 (m, 1H), 3.37–3.41 (m, 2H), 3.11–3.16 (m, 2H), 2.00–2.02 (m, 2H), 1.57–1.62 (m, 2H), 0.79–0.84 (m, 3H); MS (M+1) 204.3.

Exo-N-[3-(6-Ethyl-3-aza-bicyclo[3.1.0]hex-6-yl)-phenyl]-methanesulfonamide

400 MHz ¹H NMR (CD₃OD) δ 7.29 (t, 1H), 7.19–7.22 (m, 1H), 7.09–7.12 (m, 1H), 3.71–3.78 (m, 2H), 3.28–3.31 (m, 2H), 2.95 (s, 3H), 2.30–2.38 (m, 2H), 1.59–1.64 (m, 2H), 0.86 (t, 3H).

Exo-3-(6-Ethyl-3-aza-bicyclo[3.1.0]hex-6-yl)-benzamide

400 MHz ¹H NMR (CD₃OD) δ 7.61–7.80 (m, 2H), 7.26–7.41 (m, 2H), 3.21–3.33 (m, 2H), 3.12–3.20 (m, 2H), 1.88–1.97 (m, 2H), 1.77–1.83 (m, 2H), 0.79 (t, 3H); MS (M+1) 231.3.

Exo-1-Methyl-1H-imidazole-4-sulfonic acid [3-(6-ethyl-3-aza-bicyclo[3.1.0]hex-6-yl)-phenyl]-amide 400 MHz ¹H NMR (CD₃OD) δ 7.65 (s, 1H), 7.58 (s, 1H), 7.09–7.13 (m, 1H), 7.02 (s, 1H), 6.92–6.97 (m, 1H), 3.65 (s, 3H), 3.41–3.49 (m, 2H), 3.15–3.18 (m, 2H), 2.01–2.03 (m, 2H), 1.53–1.58 (m, 2H), 0.72 (t, 3H); MS (M+1) 347.3.

Exo-2-Methoxy-ethanesulfonic acid [3-(6-ethyl-3-aza-bicyclo[3.1.0]hex-6-yl)-phenyl]-amide 400 MHz ¹H NMR (CD₃OD) δ 7.02–7.21 (m, 4H), 3.79–3.84 (m, 2H), 3.35–3.42 (m, 5H), 3.21–3.31 (m, 4H), 1.84–1.87 (m, 2H), 1.62–1.78 (m, 2H), 0.83 (t, 3H), MS (M+1) 325.1.

Exo-N-[3-(6-Propyl-3-aza-bicyclo[3.1.0]hex-6-yl)-phenyl]-methanesulfonamide

400 MHz $^1$H NMR (CD$_3$OD) δ 7.23–7.26 (m, 1H), 7.12–7.17 (m, 1H), 7.06–7.09 (m, 2H), 3.37–3.41 (m, 2H), 3.16 (d, J=12.0 Hz, 2H), 2.92 (s, 3H), 2.04–2.06 (m, 2H), 1.57–1.61 (m, 2H), 1.21–1.26 (m, 2H), 0.88 (t, J=7.5 Hz, 3H).

Exo-N-[3-(6-Isopropyl-3-aza-bicyclo[3.1.0]hex-6-yl)-phenyl]-ethanesulfonamide

400 MHz $^1$H NMR (CD$_3$OD) δ 7.20–7.24 (m, 1H), 7.14–7.16 (m, 1H), 7.01–7.09 (m, 2H), 3.42–3.46 (m, 2H), 3.17 (d, J=12.0 Hz, 2H), 2.90 (s, 3H), 2.07–2.09 (m, 2H), 1.58–1.65 (m, 1H), 0.89 (d, J=7.1 Hz, 6H).

Exo-3-(6-Propyl-3-aza-bicyclo[3.1.0]hex-6-yl)-benzamide

400 MHz $^1$H NMR (CD$_3$OD) δ 7.77–7.79 (m, 1H), 7.67–7.70 (m, 1H), 7.43–7.46 (m, 1H), 7.34–7.38 (m, 1H), 3.47–3.52 (m, 2H), 3.20 (d, J=12.4 Hz, 2H), 2.14–2.16 (m, 2H), 1.57–1.61 (m, 2H), 1.16–1.22 (m, 2H), 0.85 (t, J=7.5 Hz, 3H).

Exo-Ethanesulfonic acid [3-(6-ethyl-3-aza-bicyclo[3.1.0]hex-6-yl)-phenyl]-amide

400 MHz $^1$H NMR (CD$_3$OD) δ 7.01–7.21 (m, 4H), 3.18–3.21 (m, 2H), 2.99–3.05 (m, 4H), 1.88–1.90 (m, 2H), 1.63 (q, J=7.5 Hz, 2H), 1.25 (t, J=7.5 Hz, 3H), 0.81 (t, J=7.5 Hz, 3H); MS (M+1) 295.2.

Example 7

General Procedure For the Reductive Alkylation Preparation of Compounds of Formula (XXII)

To a stirring solution of 1.0 equiv. of a compound of formula XVIII in methylene chloride (0.2 M) at room temperature was added an aldehyde of formula XIX (2.0 equiv.), acetic acid (2.0 equiv.) and sodium triacetoxyborohydride (2.0 equiv.). The reaction mixtures were stirred at room temperature for up to 24 hours. The mixtures were then quenched by the addition of saturated sodium bicarbonate solution and extracted with methylene chloride. The combined organic layers were dried over anhydrous MgSO$_4$ and concentrated under reduced pressure. The resulting crude material was purified by flash chromatography to yield the desired tertiary amines in 40–95% yield.

The following compounds were made using the above procedure of Example 7, starting with the appropriate starting amine of formula (XVIII) and the appropriate aldehyde reagent of formula (XIX).

Furthermore, pharmaceutically acetable salts of the compounds listed below can be prepared as follows. To a stirring solution of compounds of the general formula (XXII) (prepared as described above in Example 7, 1.0 equiv.) in a suitable solvent such as methyl ethyl ketone, methylene chloride/methanol (1:1) or methanol (0.1 M) at room temperature was added the appropriate acid, such as citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

Exo-N-(3-{6-Ethyl-3-[3-(1-hydroxy-cyclohexyl)-propyl]-3-aza-bicyclo[3.1.0]hex-6-yl}-phenyl)-methanesulfonamide 400 MHz $^1$H NMR (CDCl$_3$) δ 7.16–7.23 (m, 2H), 6.98–7.09 (m, 3H), 2.94–2.97 (m, 4H), 2.81–2.84 (m, 2H), 2.516 (s, 2H), 1.21–1.94 (m, 16H), 0.76 (t, J=7.4, 3H); MS (m+1)421.2.

Exo-N-(3-{6-Ethyl-3-[3-(1-hydroxy-cyclohexyl)-propyl]-3-aza-bicyclo[3.1.0]hex-6-yl}-phenyl)-methanesulfonamide citrate, m.p. 85–90° C.

Exo-N-(3-{6-Ethyl-3-[3-(1-hydroxymethyl-cyclopentyl)-propyl]-3-aza-bicyclo[3.1.0]hex-6-yl}-phenyl)-methanesulfonamide 400 MHz $^1$H NMR (CDCl$_3$) δ 7.19–7.23 (m, 1H), 7.09 (m, 1H), 7.02–7.05 (m, 2H), 3.37 (s, 2H), 3.00–3.02 (m, 2H), 2.97 (s, 3H), 2.86–2.89 (m, 2H), 2.50–2.53 (m, 2H), 1.80–1.85 (m, 4H), 1.53–1.59 (m, 4H), 1.31.1.48 (m, 5H), 1.28–1.20 (m, 3H), 0.78 (t, J=7.6, 3H); MS (m+1) 421.2.

Exo-1-{3-[6-(3,5-Difluoro-phenyl)-6-ethyl-3-aza-bicyclo[3.1.0]hex-3-yl]-propyl}-cyclohexanol 400 MHz $^1$H NMR (CDCl$_3$) δ 6.68–6.74 (m, 2H), 6.54–6.6 (m, 1H), 2.87–2.93 (m, 4H), 2.49–2.52 (m, 2H), 1.76–1.96 (m, 4H), 1.19–1.66 (m, 14H), 0.80 (t, J=7.4, 3H); MS (m+1) 364.2.

Exo-3-{6-Ethyl-3-[3-(1-hydroxy-cyclohexyl)-propyl]-3-aza-bicyclo[3.1.0]hex-6-yl}-benzamide 400 MHz $^1$H NMR (CDCl$_3$) δ 7.69 (s, 1H), 7.57–7.59 (m, 1H), 7.23–7.32 (m, 2H), 6.67 (s, 1H), 6.34 (s, 1H), 3.01–3.04 (m, 2H), 2.84, 2.87 (m, 2H), 2.54–2.57 (m, 2H), 1.82–1.84 (m, 2H), 1.74–1.75 (m, 2H), 1.17–1.72 (m, 8H), 0.73 (t, J=7.2, 3H); MS (m+1) 371.2.

Exo-2-Methoxy-ethanesulfonic acid (3-{6-ethyl-3-[3-(1-hydroxy-cyclohexyl)-propyl]-3-aza-bicyclo[3.1.0]hex-6-yl}-phenyl)-amide 400 MHz $^1$H NMR (CDCl$_3$) δ 7.19 (t, J=8.0, 1H), 7.11 (s, 1H), 7.0–7.9 (m, 2H), 3.78–3.80 (m, 2H), 3.37 (s, 3H), 3.18–3.21 (m, 2H), 2.88–2.95 (m, 4H), 2.53 (s, 2H), 1.73–1.83 (m, 4H), 1.19–1.62 (m, 14H), 0.79 (t, J=7.4, 3H); MS (m+1) 465.1.

Exo-2-Methoxy-ethanesulfonic acid (3-{6-ethyl-3-[3-(1-hydroxy-cyclohexyl)-propyl]-3-aza-bicyclo[3.1.0]hex-6-yl}-phenyl)-amide citrate, m.p. 120–124° C.

Exo-N-(3-{6-Ethyl-3-[3-(1-hydroxy-cyclohexyl)-propyl]-3-aza-bicyclo[3.1.0]hex-6-yl}-5-fluoro-phenyl)-methanesulfonamide 400 MHz $^1$H NMR (CDCl$_3$) δ 6.84–6.88 (m, 2H), 6.68–6.71 (m, 1H), 2.97.2.99 (m, 5H), 2.82–2.85 (m, 2H), 2.54 (s, 2H), 1.73–1.78 (m, 4H), 1.23–1.64 (m, 14H), 0.78 (t, J=7.4, 3H): MS (m+1) 439.3.

Exo-N-(3-{6-Ethyl-3-[3-(1-hydroxy-cyclohexyl)-propyl]-3-aza-bicyclo[3.1.0]hex-6-yl}-5-fluoro-phenyl)-methanesulfonamide besylate, m.p. 85–88° C.

Exo-3-{6-Ethyl-3-[3-(1-hydroxy-cyclohexyl)-propyl]-3-aza-bicyclo[3.1.0]hex-6-yl}-5-fluoro-benzamide 400 MHz $^1$H NMR (CDCl$_3$) δ 7.47 (m, 1H), 7.28–7.31 (m, 1H), 7.04–7.07 (m, 1H), 6.38 (s, 1H), 5.98 (s, 1H), 3.02–3.04 (m, 2H), 2.88–2.91 (m, 2H), 2.57 (m, 2H), 1.87–1.88 (m, 2H), 1.76–1.81 (m, 2H), 1.19–1.624 (m, 14H), 0.780 (t, J=7.4); MS (m+1) 389.2.

Exo-3-{6-Ethyl-3-[3-(1-hydroxy-cyclohexyl)-propyl]-3-aza-bicyclo[3.1.0]hex-6-yl}-5-fluoro-benzamide tosylate, m.p. 118–123° C.

Exo-1-Methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide 400 MHz $^1$H NMR (CDCl$_3$) δ 7.44 (s, 1H), 7.22–7.23 (m, 1H), 7.07–7.10 (m, 1H), 7.02–7.05 (m, 2H), 6.90–6.92 (m, 1H), 3.58 (s, 3H), 3.44 (s, 2H), 2.91–2.94 (m, 2H), 2.80–2.83 (m, 2H), 2.50 (s, 2H), 1.21–1.76 (m, 17H), 0.64 (t, J=7.4); MS (m+1) 487.2.

Exo-1-Methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide citrate, m.p. 145–148° C.

Exo-3-{6-Ethyl-3-[3-(1-hydroxy-cyclohexyl)-propyl]-3-aza-bicyclo[3.1.0]hex-6-yl}-phenol 400 MHz $^1$H NMR (CDCl$_3$) δ 7.03 (t, J=7.6, 1H), 6.63–6.67 (m, 3H), 3.04–3.07 (m, 2H), 2.61–2.64 (m, 2H), 2.52 (s, 2H), 1.72–1.75 (m, 2H), 1.17–1.65 (m, 17H), 7.6 (t, J=7.2, 3H); MS (m+1) 344.3.

Exo-3-{6-Ethyl-3-[3-(1-hydroxy-cyclohexyl)-propyl]-3-aza-bicyclo[3.1.0]hex-6-yl}-phenol citrate, m.p. 147–152° C.

Exo-N-(3-{6-Ethyl-3-[3-(1-nitro-cyclohexyl)-propyl]-3-aza-bicyclo[3.1.0]hex-6-yl}-phenyl)-methanesulfonamide 400 MHz $^1$H NMR (CDCl$_3$) δ 7.21–7.26 (m, 1H), 7.02–7.11 (m, 3H), 2.99 (s, 3H), 2.94–2.96 (m, 2H), 2.69–2.73 (m, 2H), 2.38–2.43 (m, 4H), 1.93 (q, J=7.47 Hz, 2H), 1.83–1.87 (m, 2H), 1.73–1.75 (m, 2H), 1.54–1.65 (m, 5H), 1.31–1.48 (m, 5H), 0.81 (t, J=7.5 Hz, 3H); MS (M+1) 450.3.

Exo-N-(3-{3-[3-(1-Amino-cyclohexyl)-propyl]-6-ethyl-3-aza-bicyclo[3.1.0]hex-6-yl}-phenyl)-methanesulfonamide 400 MHz $^1$H NMR (CDCl$_3$) δ 7.14–7.17 (m, 1H), 6.98–7.05 (m, 3H), 3.26–3.35 (brs, 3H), 2.92 (s, 3H), 2.86–2.89 (m, 2H), 2.73–2.75 (m, 2H), 2.36–2.39 (m, 2H), 1.83–1.89 (m, 2H), 1.69 (s, 2H), 1.21–1.39 (m, 14H), 0.73–0.76 (m, 3H); MS (M+1) 420.3.

Exo-N-(1-{3-[6-Ethyl-6-(3-methanesulfonylamino-phenyl)-3-aza-bicyclo[3.1.0]hex-3-yl]-propyl}-cyclohexyl)-acetamide 400 MHz $^1$H NMR (CDCl$_3$) δ 7.19–7.23 (m, 1H), 7.12–7.13 (m, 1H), 7.04–7.07 (m, 2H), 5.29 (s, 1H), 2.97 (s, 3H), 2.83–2.90 (m, 4H), 2.43 (t, J=7.5 Hz, 2H), 2.01–2.05 (m, 2H), 1.97 (s, 3H), 1.87 (q, J=7.5 Hz, 2H), 1.75–1.79 (m, 4H), 1.25–1.52 (m, 10H), 0.79 (t, J=7.9 Hz, 3H); MS (M+1) 462.3.

Exo-N-(3-{6-Ethyl-3-[2-(2-hydroxy-indan-2-yl)-ethyl]-3-aza-bicyclo[3.1.0]hex-6-yl}-phenyl)-methanesulfonamide 400 MHz $^1$H NMR (CDCl$_3$) δ 6.99–7.21 (m, 8H), 2.94–3.14 (m, 8H), 2.93 (s, 3H), 2.88–2.91 (m, 2H), 1.85 (brs, 4H), 1.65 (q, J=7.5 Hz, 2H), 0.76 (t, J=7.5 Hz, 3H); MS (M+1) 441.2.

Exo-3-{6-Ethyl-3-[2-(2-hydroxy-indan-2-yl)-ethyl]-3-aza-bicyclo[3.1.0]hex-6-yl}-benzamide 400 MHz $^1$H NMR (CDCl$_3$) δ 7.69–7.71 (m, 1H), 7.52–7.55 (m, 1H), 7.35–7.37 (m, 1H), 7.27–7.31 (m, 1H), 7.07–7.16 (m, 4H), 6.18 (brs, 1H), 5.92 (brs, 1H), 2.93–3.11 (m, 8H), 2.86–2.88 (m, 2H), 1.81–1.87 (m, 4H), 1.68 (q, J=7.5 Hz, 2H), 0.76 (t, J=7.5 Hz, 3H); MS (M+1) 391.1.

Exo-3-{3-[3-(1-Hydroxy-cyclohexyl)-propyl]-6-propyl-3-aza-bicyclo[3.1.0]hex-6-yl}-benzamide 400 MHz $^1$H NMR (CDCl$_3$) δ 7.69–7-70 (m, 1H), 7.53–7.56 (m, 1H), 7.34–7.37 (m, 1H), 7.26–7.30 (m, 1H), 6.24 (brs, 1H), 6.00 (brs, 1H), 2.90 (s, 4H), 2.50–2.53 (m, 2H), 1.82 (s, 2H), 1.69–1.73 (m, 2H), 1.12–1.59 (m, 16H), 0.82 (t, J=7.5 Hz, 3H); MS (M+1) 385.5.

Exo-N-(3-{3-[3-(1-Hydroxy-cyclohexyl)-propyl]-6-propyl-3-aza-bicyclo[3.1.0]hex-6-yl}-phenyl)-methanesulfonamide 400 MHz $^1$H NMR (CDCl$_3$) δ 7.15–7.19 (m, 1H), 7.06 (s, 1H), 6.98–7.02 (m, 2H), 2.93 (s, 5H), 2.79–2.82 (m, 2H), 2.50 (s, 2H), 1.77–1.78 (m, 2H), 1.12–1.66 (m, 18H), 0.81 (t, J=7.5 Hz, 3H); MS (M+1) 435.3.

Exo-N-(3-{3-[3-(1-Cyano-cyclohexyl)-propyl]-6-ethyl-3-aza-bicyclo[3.1.0]hex-6-yl}-phenyl)-methanesulfonamide 400 MHz $^1$H NMR (CDCl$_3$) δ 7.18–7.22 (m, 1H), 7.00–7.09 (m, 3H), 2.95–2.97 (m, 5H), 2.77–2.78 (m, 2H), 2.45–2.48 (m, 2H), 1.87–1.96 (m, 4H), 1.50–1.74 (m, 11H), 1.12–1.22 (m, 3H), 0.78 (t, J=7.5 Hz, 3H); MS (M+1) 430.3.

Exo-2-Methoxy-ethanesulfonic acid (3-{3-[3-(1-hydroxy-cyclohexyl)-propyl]-6-propyl-3-aza-bicyclo[3.1.0]hex-6-yl}-phenyl)-amide 400 MHz $^1$H NMR (CDCl$_3$) δ 7.18 (t, J=7.9 Hz, 1H), 7.09–7.10 (m, 1H), 6.99–7.03 (m, 2H), 3.79 (t, J=5.4 Hz, 2H), 3.45 (s, 3H), 3.18 (t, J=5.4 Hz, 2H), 3.08 (brs, 2H), 3.06 (brs, 2H), 2.90 (brs, 2H), 1.87 (brs, 2H), 1.15–1.67 (m, 18H), 0.84 (t, J=7.5 Hz, 3H); MS (M+1) 479.3.

Exo-3-{3-[3-(1-Cyano-cyclohexyl)-propyl]-6-ethyl-3-aza-bicyclo[3.1.0]hex-6-yl}-benzamide 400 MHz $^1$H NMR (CDCl$_3$) δ 7.70–7.71 (m, 1H), 7.54–7.56 (m, 1H), 7.37–7.39 (m, 1H), 7.28–7.31 (m, 1H), 6.20 (brs, 1H), 6.02 (brs, 1H), 2.98 (d, J=9.5 Hz, 2H), 2.75–2.77 (m, 2H), 2.44–2.47 (m, 2H), 1.90–1.95 (m, 4H), 1.74–1.79 (m, 2H), 1.50–1.72 (m, 9H), 1.09–1.22 (m, 3H), 0.76 (t, J=7.5 Hz, 3H); MS (M+1) 380.3.

Exo-N-(3-{3-[3-(1-Cyano-cyclopentyl)-propyl]-6-ethyl-3-aza-bicyclo[3.1.0]hex-6-yl}-phenyl)-methanesulfonamide 400 MHz $^1$H NMR (CDCl$_3$) δ 7.19–7.21 (m, 1H), 7.01–7.09 (m, 3H), 2.94–2.96 (m, 5H), 2.84–2.86 (m, 2H), 2.49–2.52 (m, 2H), 2.09–2.14 (m, 2H), 1.53–2.08 (m, 14H), 0.78 (t, J=7.5 Hz, 3H); MS (M+1) 416.1.

Exo-3-{3-[3-(1-Cyano-cyclopentyl)-propyl]-6-ethyl-3-aza-bicyclo[3.1.0]hex-6-yl}-benzamide 400 MHz $^1$H NMR (CDCl$_3$) δ 7.70–7.71 (m, 1H), 7.54–7.56 (m, 1H), 7.36–7.38 (m, 1H), 7.23–7.30 (m, 1H), 6.27 (brs, 1H), 6.21 (brs, 1H), 2.97 (d, J=9.5 Hz, 2H), 2.74–2.77 (m, 2H), 2.44–2.47 (m, 2H), 2.06–2.12 (m, 2H), 1.91 (q, J=7.5 Hz, 2H), 1.52–1.84 (m, 12H), 0.75 (t, J=7.5 Hz, 3H); MS (M+1) 366.3.

Exo-2-Methoxy-ethanesulfonic acid (3-{3-[3-(1-cyano-cyclopentyl)-propyl]-6-ethyl-3-aza-bicyclo[3.1.0]hex-6-yl}-phenyl)-amide 400 MHz $^1$H NMR (CDCl$_3$) δ 7.16–7.20(m, 1H), 7.10–7.11 (m, 1H), 7.00–7.05 (m, 2H), 3.78 (t, J=5.4 Hz, 2H), 3.36 (s, 3H), 3.20 (t, J=5.4 Hz, 2H), 2.96 (d, J=9.5 Hz, 2H), 2.77–2.79 (m, 2H), 2.46–2.49 (m, 2H), 2.07–2.13 (m, 2H), 1.89 (q, J=7.5 Hz, 2H), 1.52–1.83 (m, 12H), 0.78 (t, J=7.5 Hz, 3H); MS (M+1) 460.3.

Exo-N-(1-{3-[6-Ethyl-6-(3-methanesulfonylaminophenyl)-3-aza-bicyclo[3.1.0]hex-3-yl]-propyl}-cyclohexyl)-benzamide 400 MHz $^1$H NMR (CDCl$_3$) δ 7.69–7.71 (m, 2H), 7.36–7.46 (m, 3H), 7.14–7.18 (m, 1H), 7.08–7.09 (m, 1H), 6.99–7.04 (m, 2H), 5.79 (s, 1H), 2.91 (s, 3H), 2.83 (s, 4H), 2.42–2.46 (m, 2H), 2.16–2.18 (m, 2H), 1.79–1.88 (m, 4H), 1.72 (s, 2H), 1.27–1.57 (m, 10H), 0.74 (t, J=7.5 Hz, 3H); MS (M+1) 524.3.

Exo-N-(1-{3-[6-Ethyl-6-(3-methanesulfonylaminophenyl)-3-aza-bicyclo[3.1.0]hex-3-yl]-propyl}-cyclohexyl)-isobutyramide 400 MHz $^1$H NMR (CDCl$_3$) δ 7.17–7.21 (m, 1H), 7.09–7.11 (m, 1H), 7.00–7.05 (m, 2H), 5.06 (s, 1H), 2.95 (s, 3H), 2.87 (s, 4H), 2.44 (brs, 2H), 2.27–2.34 (m, 1H), 2.02–2.05 (m, 2H), 1.83 (q, J=7.5 Hz, 2H), 1.71–1.76 (m, 4H), 1.16–1.55 (m, 10H), 1.11 (d, J=6.6 Hz, 6H), 0.76 (t, J=7.5 Hz, 3H); MS (M+1) 490.4.

Exo-N-(3-{3-[3-(1-Hydroxy-cyclohexyl)-propyl]-6-isopropyl-3-aza-bicyclo[3.1.0]hex-6-yl}-phenyl)-methanesulfonamide 400 MHz $^1$H NMR (CDCl$_3$) δ 7.17–7.21 (m, 1H), 6.98–7.06 (m, 3H), 3.09–3.12 (m, 2H), 2.95 (s, 3H), 2.82–2.84 (m, 2H), 2.57 (brs, 2H), 1.95–1.97 (m, 1H), 1.84 (s, 2H), 1.19–1.64 (m, 14H), 0.81 (d, J=7.1 Hz, 6H); MS (M+1) 435.3.

Exo-2-Methoxy-ethanesulfonic acid (3-{3-[3-(1-hydroxy-cyclohexyl)-propyl]-6-isopropyl-3-aza-bicyclo[3.1.0]hex-6-yl}-phenyl)-amide 400 MHz $^1$H NMR (CDCl$_3$) δ 7.15–7.19 (m, 1H), 6.99–7.08 (m, 3H), 3.78 (t, J=5.4 Hz, 2H), 3.37 (s, 3H), 3.18 (t, J=5.4 Hz, 2H), 3.03–3.05 (m, 2H), 2.83–2.86 (m, 2H), 2.55 (s, 2H), 1.95–1.99 (m, 1H), 1.85 (s, 2H), 1.22–1.64 (m, 14H), 0.81 (d, J=7.1 Hz, 6H); MS (M+1) 4.79.3.

Exo-N-(3-{3-[3-cis-(3-Bromo-phenyl)-3-hydroxy-cyclobutylmethyl]-6-ethyl-3-aza-bicyclo[3.1.0]hex-6-yl}-phenyl)-methanesulfonamide 400 MHz $^1$H NMR (CDCl$_3$) δ 7.63–7.64 (m, 1H), 7.38–7.43 (m, 2H), 7.19–7.23 (m, 2H), 7.00–7.07 (m, 3H), 3.00–3.02 (m, 2H), 2.96 (s, 3H), 2.87–2.89 (m, 2H), 2.66–2.70 (m, 4H), 2.08–2.15 (m, 3H), 1.81–1.86 (m, 4H), 0.77 (t, J=7.5 Hz, 3H); MS (M+1) 519.2, 521.3.

Exo-N-{3-[6-Ethyl-3-(cis-3-hydroxy-3-phenyl-cyclobutylmethyl)-3-aza-bicyclo[3.1.0]hex-6-yl]-phenyl}-methanesulfonamide 400 MHz $^1$H NMR (CD$_3$OD) δ 7.52–7.54 (m, 2H), 7.27–7.37 (m, 2H), 7.23–7.26 (m, 2H), 7.16–7.17 (m, 1H), 7.04–7.08 (m, 2H), 3.82–3.86 (m, 2H), 3.30–3.32 (m, 2H), 3.03–3.06 (m, 2H), 2.90 (s, 3H), 2.77–2.82 (m, 2H), 2.15–2.26 (m, 5H), 1.73–1.79 (m, 2H), 0.83 (t, J=7.5 Hz, 3H); MS (M+1) 441.3.

Exo-3-{3-[3-cis-(3-Bromo-phenyl)-3-hydroxy-cyclobutylmethyl]-6-ethyl-3-aza-bicyclo[3.1.0]hex-6-yl}-benzamide 400 MHz $^1$H NMR (CD$_3$OD) δ 7.75–7.76 (m, 1H), 7.65–7.67 (m, 2H), 7.32–7.50 (m, 4H), 7.24–7.28 (m, 1H), 3.09–3.12 (m, 2H), 2.85–2.88 (m, 2H), 2.74–2.76 (m, 2H), 2.61–2.65 (m, 2H), 2.05–2.07 (m, 3H), 1.94–1.95 (m, 3H), 1.87 (q, J=7.5 Hz, 2H), 0.78 (t, J=7.5 Hz, 3H); MS (M+1) 471.2.

Exo-3-[6-Ethyl-3-(cis-3-hydroxy-3-phenyl-cyclobutylmethyl)-3-aza-bicyclo[3.1.0]hex-6-yl]-benzamide 400 MHz $^1$H NMR (CD$_3$OD) δ 7.78 (s, 1H), 7.71–7.73 (m, 1H), 7.52–7.55 (m, 2H), 7.34–7.52 (m, 4H), 7.24–7.27 (m, 1H), 3.94 (brs, 2H), 3.38–3.40 (m, 2H), 3.09 (brs, 2H), 2.79–2.82 (m, 2H), 2.33–2.35 (m, 2H), 2.17–2.29 (m, 3H), 1.78 (q, J=7.5 Hz, 2H), 0.83 (t, J=7.5 Hz, 3H); MS (M+1) 391.2.

Exo-3-{6-Ethyl-3-[3-(1-hydroxymethyl-cyclopentyl)-propyl]-3-aza-bicyclo[3.1.0]hex-6-yl}-benzamide 400 MHz $^1$H NMR (CDCl$_3$) δ 7.70 (s, 1H), 7.54–7.56 (m, 1H), 7.34–7.38 (m, 1H), 7.27–7.31 (m, 1H), 6.29 (brs, 1H), 6.02 (brs, 1H), 3.35 (s, 2H), 2.87 (s, 4H), 2.42–2.45 (m, 2H), 1.80–1.88 (m, 4H), 1.51–1.54 (m, 4H), 1.29–1.50 (m, 8H), 0.73–0.77 (m, 3H); MS (M+1) 371.3.

Exo-N-(3-{3-[3-(1-Hydroxymethyl-cyclopentyl)-propyl]-6-isopropyl-3-aza-bicyclo[3.1.0]hex-6-yl}-phenyl)-methanesulfonamide 400 MHz $^1$H NMR (CDCl$_3$) δ 7.16–7.20 (m, 1H), 7.05–7.07 (m, 2H), 6.97–6.99 (m, 1H), 3.36 (s, 2H), 3.12–3.14 (m, 2H), 2.95 (s, 3H), 2.79–2.82 (m, 2H), 2.52–2.55 (m, 2H), 2.06–2.09 (m, 1H), 1.84–1.85 (m, 2H), 1.30–1.58 (m, 12H), 0.80 (d, J=7.1 Hz, 6H); MS (M+1) 435.3.

Exo-1-[6-Ethyl-6-(3-methanesulfonylamino-phenyl)-3-aza-bicyclo[3.1.0]hex-3-ylmethyl]-cyclohexanecarboxylic acid amide 400 MHz $^1$H NMR (CDCl$_3$) δ 7.62 (brs, 1H), 7.18–7.21 (m, 1H), 7.09–7.11 (m, 1H), 6.99–7.06 (m, 2H), 6.68 (brs, 1H), 5.75 (brs, 1H), 2.99–3.08 (m, 4H), 2.96 (s, 3H), 2.66 (s, 2H), 1.81–1.92 (m, 2H), 1.75–1.79 (m, 4H), 1.43–1.53 (m, 5H), 1.19–1.31 (m, 3H), 0.79 (t, J=7.5 Hz, 3H); MS (M+1) 420.3.

Exo-N-{3-[6-Ethyl-3-(cis-1-hydroxy-3-phenyl-cyclobutylmethyl)-3-aza-bicyclo[3.1.0]hex-6-yl]-phenyl}-methanesulfonamide 400 MHz $^1$H NMR (CDCl$_3$) δ 7.02–7.29 (m, 9H), 3.12–3.16 (m, 2H), 3.02–3.10 (m, 2H), 2.97–3.00 (m, 4H), 2.88 (s, 2H), 2.47–2.52 (m, 2H), 2.29–2.34 (m, 2H), 1.80–1.89 (m, 4H), 0.80–0.84 (m, 3H); MS (M+1) 441.3.

Exo-3-[6-Ethyl-3-(cis-1-hydroxy-3-phenyl-cyclobutylmethyl)-3-aza-bicyclo[3.1.0]hex-6-yl]-benzamide 400 MHz $^1$H NMR (CDCl$_3$) δ 7.73–7.74 (m, 1H), 7.56–7.58 (m, 1H), 7.14–7.41 (m, 7H), 6.20 (brs, 1H), 5.70 (brs, 1H), 3.29–3.35 (m, 1H), 2.95–3.11 (m, 6H), 2.52–2.57 (m, 2H), 2.31–2.37 (m, 2H), 1.90–1.98 (m, 2H), 1.80–1.86 (m, 2H), 0.79–0.83 (m, 3H); MS (M+1) 391.3.

Exo-N-{3-[3-(cis-1-Hydroxy-3-phenyl-cyclobutylmethyl)-6-isopropyl-3-aza-bicyclo[3.1.0]hex-6-yl]-phenyl}-methanesulfonamide 400 MHz $^1$H NMR (CDCl$_3$) δ 7.14–7.28 (m, 6H), 7.01–7.09 (m, 3H), 3.23 (brs, 2H), 3.05–3.07 (m, 3H), 2.96 (s, 3H), 2.89 (s, 2H), 2.48–2.50 (m, 2H), 2.29–2.35 (m, 2H), 2.02–2.16 (m, 1H), 1.90 (s, 2H), 0.84 (d, J=6.6 Hz, 6H); MS (M+1) 455.3.

Exo-2-{2-[6-Ethyl-6-(3-methanesulfonylamino-phenyl)-3-aza-bicyclo[3.1.0]hex-3-yl]-ethyl}-indan-2-carboxylic acid tert-butyl ester 400 MHz $^1$H NMR (CDCl$_3$) δ 7.02–7.19 (m, 6H), 7.00–7.01 (m, 2H), 3.38 (d, J=16.2 Hz, 2H), 2.94 (s, 3H), 2.79–2.89 (m, 6H), 2.43–2.47 (m, 2H), 1.81–1.89 (m, 4H), 1.72–1.74 (m, 2H), 1.42 (s, 9H), 0.76 (t, J=7.5 Hz, 3H); MS (M+1) 525.3.

Exo-2-{2-[6-Ethyl-6-(3-methanesulfonylamino-phenyl)-3-aza-bicyclo[3.1.0]hex-3-yl]-ethyl}-indan-2-carboxylic acid 400 MHz $^1$H NMR (CDCl$_3$) δ 6.99–7.13 (m, 7H), 6.85–6.87 (m, 1H), 3.61–3.72 (m, 2H), 3.44 (d, J=16.2 Hz, 2H), 2.98–3.03 (m, 2H), 2.86–2.90 (m, 5H), 2.72 (d, J=16.2 Hz, 2H), 2.02–2.04 (m, 2H), 1.86–1.88 (m, 2H), 1.52–1.54 (m, 2H), 0.70 (t, J=7.5 Hz, 3H); MS (M+1) 469.3.

Exo-2-{2-[6-Ethyl-6-(3-methanesulfonylamino-phenyl)-3-aza-bicyclo[3.1.0]hex-3-yl]-ethyl}-indan-2-carboxylic acid amide 400 MHz $^1$H NMR (CDCl$_3$) δ 7.07–7.23 (m, 7H), 7.01–7.03 (m, 1H), 6.51 (brs, 1H), 5.78 (brs, 1H), 3.40 (d, J=16.2 Hz, 2H), 2.90–2.99 (m, 9H), 2.63–2.66 (m, 2H), 1.93–1.97 (m, 2H), 1.77–1.82 (m, 4H), 0.79 (t, J=7.5 Hz, 3H); MS (M+1) 468.3.

Exo-N-(3-{6-Ethyl-3-[2-(2-hydroxymethyl-indan-2-yl)-ethyl]-3-aza-bicyclo[3.1.0]hex-6-yl}-phenyl)-methanesulfonamide 400 MHz $^1$H NMR (CDCl$_3$) δ 7.18–7.22 (m, 1H), 7.04–7.14 (m, 6H), 6.97–6.99 (m, 1H), 3.43 (s, 2H), 3.31–3.34 (m, 2H), 2.94 (s, 3H), 2.90 (d, J=16.2 Hz, 2H), 2.71–2.77 (m, 4H), 2.66 (d, J=16.2 Hz, 2H), 1.87–1.89 (m, 2H), 1.80–1.83 (m, 2H), 1.57–1.62 (m, 2H), 0.77 (t, J=7.5 Hz, 3H); MS (M+1) 455.3.

Exo-N-(3-{6-Ethyl-3-[3-(2-nitro-indan-2-yl)-propyl]-3-aza-bicyclo[3.1.0]hex-6-yl}-phenyl)-methanesulfonamide 400 MHz $^1$H NMR (CDCl$_3$) δ 7.14–7.23 (m, 5H), 6.99–7.08 (m, 3H), 3.87 (d, J=17.0 Hz, 2H), 3.20 (d, J=17.0 Hz, 2H), 2.93–2.96 (m, 5H), 2.72–2.74 (m, 2H), 2.43–2.46 (m, 2H), 2.13–2.17 (m, 2H), 1.87 (q, J=7.5 Hz, 2H), 1.72–1.73 (m, 2H), 1.40–1.47 (m, 2H), 0.74 (t, J=7.5 Hz, 3H); MS (M+1) 484.4.

Exo-3-{6-Ethyl-3-[3-(2-nitro-indan-2-yl)-propyl]-3-aza-bicyclo[3.1.0]hex-6-yl}-benzamide 400 MHz $^1$H NMR (CDCl$_3$) δ 7.70–7.72 (m, 1H), 7.53–7.56 (m, 1H), 7.32–7.39 (m, 1H), 7.28–7.31 (m, 1H), 7.14–7.23 (m, 4H), 6.13 (brs, 1H), 5.93 (brs, 1H), 3.87 (d, J=17.0 Hz, 2H), 3.20 (d, J=17.0 Hz, 2H), 2.95 (d, J=9.5 Hz, 2H), 2.72–2.74 (m, 2H), 2.43–2.46 (m, 2H), 2.13–2.19 (m, 2H), 1.89 (q, J=7.5 Hz, 2H), 1.74–1.78 (m, 2H), 1.42–1.48 (m, 2H), 0.73 (t, J=7.5 Hz, 3H); MS (M+1) 434.4.

Exo-N-(3-{3-[3-(2-Amino-indan-2-yl)-propyl]-6-ethyl-3-aza-bicyclo[3.1.0]hex-6-yl}-phenyl)-methanesulfonamide 400 MHz $^1$H NMR (CD$_3$OD) δ 7.18–7.29 (m, 6H), 7.05–7.10 (m, 2H), 3.59–3.61 (m, 2H), 3.22 (ABq, ΔAB=42.8 Hz, J=17.0 Hz, 4H), 2.93–3.08 (m, 7H), 2.15 (s, 2H), 1.94–1.98 (m, 2H), 1.76–1.81 (m, 4H), 0.83 (t, J=7.5 Hz, 3H); MS (M+1) 454.4.

Exo-3-{3-[3-(2-Amino-indan-2-yl)-propyl]-6-ethyl-3-aza-bicyclo[3.1.0]hex-6-benzamide 400 MHz $^1$H NMR (CDCl$_3$) δ 7.69 (s, 1H), 7.54–7.56 (m, 1H), 7.33–7.35 (m, 1H), 7.23–7.28 (m, 1H), 7.10–7.13 (m, 4H), 6.51 (brs, 1H), 6.28 (brs, 1H), 2.79–2.99 (m, 10H), 2.47 (brs, 2H), 1.56–1.85 (m, 8H), 0.70–0.73 (m, 3H); MS (M+1) 404.4.

Exo-3-{3-[3-(2-Acetylamino-indan-2-y)-propyl]-6-ethyl-3-aza-bicyclo[3.1.0]hex -6-yl}-benzamide 400 MHz $^1$H NMR (CDCl$_3$) δ 7.71 (s, 1H), 7.54–7.56 (m, 1H), 7.36–7.38 (m, 1H), 7.30–7.32 (m, 1H), 7.10–7.15 (m, 4H), 6.25 (brs, 1H), 5.97 (s, 1H), 5.85 (brs, 1H), 3.30 (d, J=16.0 Hz, 2H), 2.95 (d, J=16.0 Hz, 2H), 2.86–2.91 (m, 4H), 2.46–2.50 (m, 2H), 1.94–1.98 (m, 2H), 1.88 (s, 3H), 1.83–1.86 (m, 4H), 1.44–1.49 (m, 2H), 0.74 (t, J=7.5 Hz, 3H); MS (M+1) 445.4.

Exo-N-(2-{3-[6-Ethyl-6-(3-methanesulfonylamino-phenyl)-3-aza-bicyclo[3.1.0]hex-3-yl]-propyl}-indan-2-yl)-acetamide 400 MHz $^1$H NMR (CDCl$_3$) δ 7.07–7.19 (m, 7H), 6.98–7.00 (m, 1H), 6.04 (s, 1H), 3.30 (d, J=16.2 Hz, 2H), 3.00–3.05 (m, 2H), 2.83–2.94 (m, 7H), 2.53–2.57 (m, 2H), 1.91–1.97 (m, 2H), 1.89 (s, 3H), 1.74–1.86 (m, 4H), 1.52–1.54 (m, 2H), 0.75 (t, J=7.5 Hz, 3H); MS (M+1) 496.4.

Exo-Ethanesulfonic acid (3-{6-ethyl-3-[3-(1-hydroxy-cyclohexyl)-propyl]-3-aza-bicyclo[3.1.0]hex-6-yl}-phenyl)-amide 400 MHz $^1$H NMR (CDCl$_3$) δ 7.15–7.19 (m, 1H), 7.07–7.08 (m, 1H), 7.01–7.04 (m, 1H), 6.96–6.98 (m, 1H), 3.06 (q, J=7.5 Hz, 2H), 2.96–2.98 (m, 2H), 2.84 (d, J=10.4 Hz, 2H), 2.51–2.52 (m, 2H), 1.78–1.80 (m, 2H), 1.72 (q, J=7.5 Hz, 2H), 1.43–1.64 (m, 9H), 1.29–1.42 (m, 8H), 0.76 (t, J=7.5 Hz, 3H); MS (M+1) 435.4.

Example 8

General Procedure For the Preparation of Compounds of Formula (XXIII)

To a stirring solution of a compound of formula (XVIII) in ethanol (0.1 M) at room temperature was added triethyl amine (3 equiv.) and the appropriate reagent of formula (XXI) (1.2 equiv.). The resulting mixture is heated to 80° C. for 1–5 hours and then cooled to room temperature. The mixture is concentrated under reduced pressure and the resulting crude material was purified by flash chromatography to yield the desired tertiary amines in 50–90% yield.

The following compounds were made using the above procedure of Example 8, starting with the appropriate starting amine of formula (XVIII) and the appropriate reagent of formula (XXI).

Furthermore, pharmaceutically acetable salts of the compounds listed below can be prepared as follows. To a stirring solution of compounds of the general formula (XXIII) (prepared as described above in Example 8, 1.0 equiv.), in a suitable solvent such as methyl ethyl ketone, methylene chloride/methanol (1:1) or methanol (0.1 M) at room temperature was added the appropriate acid, such as citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

Exo-3-[6-Ethyl-3-(2-hydroxy-indan-2-ylmethyl)-3-aza-bicyclo[3.1.0]hex-6-yl]-5-fluoro-benzamide 400 MHz $^1$H NMR (CDCl$_3$) δ 7.52–7.53 (m, 1H), 7.29–7.23 (m, 1H), 7.11–7.23 (m, 5H), 6.18–6.25 (m, 2H), 3.22–3.2 (m, 2H), 3.06–3.11 (m, 2H), 2.95–3.00 (m, 4H), 2.83 (s, 2H), 1.86–1.95 (m, 4H), 0.82–0.83 (m, 3H).

Exo-N-{3-[6-Ethyl-3-(2-hydroxy-indan-2-ylmethyl)-3-aza-bicyclo[3.1.0]hex-6-yl]-phenyl}-methane-sulfonamide 400 MHz $^1$H NMR (CDCl$_3$) δ 7.10–7.25 (m, 7H), 6.99–7.05 (m, 1H), 3.19–3.22 (m, 2H), 3.06–3.09 (m, 2H), 2.96–2.98 (m, 7H), 2.81 (s, 2H), 1.83–1.90 (m, 4H), 0.830 (t, J=7.4, 3H); MS (m+1) 427.1.

Exo-N-{3-[6-Ethyl-3-(2-hydroxy-indan-2-ylmethyl)-3-aza-bicyclo[3.1.0]hex-6-yl]-phenyl}-methanesulfonamide mesylate, m.p. 210–230° C.

Exo-3-[6-Ethyl-3-(2-hydroxy-indan-2-ylmethyl)-3-aza-bicyclo[3.1.0]hex-6-yl]-benzamide 400 MHz $^1$H NMR (CD$_3$OD) δ 7.76 (s, 1H), 7.63–7.65 (m, 1H), 7.41–7.44 (m, 1H) 7.31–7.35 (m, 1H), 7.12–7.14 (m, 2H), 7.0–7.09 (m, 2H), 3.18–3.28 (m, 2H), 3.05–3.10 (m, 2H), 2.98–3.00 (m, 2H), 2.86–2.89 (m, 2H), 2.73 (s, 2H), 1.94–1.99 (m, 2H), 1.81–1.84 (m, 2H), 0.79 (t, J=7.4, 3H).

Exo-3-[6-Ethyl-3-(2-hydroxy-indan-2-ylmethyl)-3-aza-bicyclo[3.1.0]hex-6-yl]-benzamide citrate, m.p. 120–124° C.

Exo-2-Methoxy-ethanesulfonic acid {3-[6-ethyl-3-(2-hydroxy-indan-2-ylmethyl)-3-aza-bicyclo[3.1.0]hex-6-yl]-phenyl}-amide 400 MHz $^1$H NMR (CDCl$_3$) δ 7.10–7.27 (m, 6H), 7.00–7.07 (m, 2H), 3.75–3.78 (m, 2H), 3.34 (s, 3H), 3.18–3.23 (m, 4H), 3.01–3.0 (m, 2H), 2.93–2.97 (m, 4H), 2.800 (s, 2H), 1.80–1.89 (m, 4H), 0.82–0.89 (m, 3H); MS (m+1) 471.2.

Exo-N-{3-[6-Ethyl-3-(2-hydroxy-indan-2-ylmethyl)-3-aza-bicyclo[3.1.0]hex-6-yl]-5-fluoro-phenyl}-methanesulfonamide 400 MHz $^1$H NMR (CDCl$_3$) δ 7.19–7.20 (m, 2H), 7.11–7.18 (m, 2H), 6.83–6.84 (m, 1H), 6.73–6.80 (m, 2H), 3.19–3.21 (m, 2H), 3.05–3.15 (m, 2H), 2.94–3.02 (m &H), 2.81 (s, 2H), 1.79–1.90 (m, 4H), 0.84 (t, J=7.4, 3H); MS (m+1) 445.3.

Exo-1-Methyl-1H-imidazole-4-sulfonic acid {3-[6-ethyl-3-(2-hydroxy-indan-2-ylmethyl)-3-aza-bicyclo[3.1.0]hex-6-yl]-phenyl}-amide 400 MHz $^1$H NMR (CDCl$_3$) δ 7.45 (s, 1H), 7.26 (s, 1H), 7.05–7.23 (m, 7H), 6.95, 6.97 (m, 1H), 3.59 (s, 3H), 3.15–3.17 (m, 2H), 3.01–3.06 (m, 2H), 2.96 (s, 2H), 1.73–1.82 (m, 4H), 0.670.72 (m, 3H); MS (m+1)493.1.

Exo-2-[6-Ethyl-6-(3-hydroxy-phenyl)-3-aza-bicyclo[3.1.0]hex-3-ylmethyl]-indan-2-ol 400 MHz $^1$H NMR (CDCl$_3$) δ 707–7.21 (m, 5H), 6.76–6.80 (m, 1H), 7.1–7.2 (m, 1H), 6.61–6.64 (m, 1H), 3.12–3.21 (m, 5H), 3.03–3.10 (m, 4H), 2.86 (s, 2H), 1.78–1.86 (m, 4H), 0.853 (m, 3H); MS (m+1) 496.3.

(+/−)-Exo-N-{3-[6-Ethyl-3-(2-hydroxy-1,2,3,4-tetrahydro-naphthalen-2-ylmethyl)-3-aza-bicyclo[3.1.0]hex-6-yl]-phenyl}-methanesulfonamide 400 MHz $^1$H NMR (CDCl$_3$) δ 7.20–7.24 (m, 2H), 6.96–7.09 (m, 6H), 3.13–3.18 (m, 3H), 2.99–3.06 (m, 1H), 2.97 (s, 3H), 2.68–2.78 (m, 5H), 1.82–1.94 (m, 5H), 1.69–1.73 (m, 2H), 0.82 (t, J=7.5 Hz, 3H); MS (M+1) 441.3.

(+/−)-Exo-2-Methoxy-ethanesulfonic acid {3-[6-ethyl-3-(2-hydroxy-1,2,3,4-tetrahydro-naphthalen-2-ylmethyl)-3-aza-bicyclo[3.1.0]hex-6-yl]-phenyl}-amide 400 MHz $^1$H NMR (CDCl$_3$) δ 7.05–7.21 (m, 8H), 3.78–3.81 (m, 2H), 3.38 (s, 3H), 2.98–3.21 (m, 8H), 2.77–2.79 (m, 2H), 2.65–2.66 (m, 2H), 1.83–1.86 (m, 6H), 0.83 (t, J=7.5 Hz, 3H); MS (M+1) 485.3.

(+/−)-Exo-1-Methyl-1H-imidazole-4-sulfonic acid {3-[6-ethyl-3-(2-hydroxy-1,2,3,4-tetrahydro-naphthalen-2-ylmethyl)-3-aza-bicyclo[3.1.0]hex-6-yl]-phenyl}-amide 400 MHz $^1$H NMR (CDCl$_3$) δ 7.44 (s, 1H), 7.25 (s, 1H), 7.02–7.12 (m, 7H), 6.94–6.96 (m, 1H), 3.60 (s, 3H), 2.98–3.16 (m, 5H), 2.72–2.83 (m, 3H), 2.65 (brs, 2H), 1.67–1.86 (m, 8H), 0.69 (t, J=7.5, 3H), MS (M+1) 507.3.

(+/−)-Exo-3-[6-Ethyl-3-(2-hydroxy-1,2,3,4-tetrahydro-naphthalen-2-ylmethyl)-3-aza-bicyclo[3.1.0]hex-6-yl]-benzamide 400 MHz $^1$H NMR (CDCl$_3$) δ 7.73 (s, 1H), 7.53–7.56 (m, 1H), 7.39–7.41 (m, 1H), 7.29–7.33 (m, 1H), 7.02–7.09 (m, 4H), 6.13 (brs, 1H), 5.89 (brs, 1H), 2.98–3.22 (m, 6H), 2.73–2.83 (m, 2H), 2.61–2.69 (m, 2H), 1.81–1.91 (m, 6H), 0.81 (t, J=7.5 Hz, 3H); MS (M+1) 391.3.

Exo-N{3-Cyano-5-[6-ethyl-3-(2-hydroxy-indan-2-ylmethyl)-3-aza-bicyclo[3.1.0]hex-6-yl]-phenyl}-methanesulfonamide 400 MHz $^1$H NMR (CDCl$_3$) δ 7.25–7.32 (m, 3H), 7.11–7.19 (m, 5H), 3.21–3.24 (m, 2H), 3.00–3.08 (m, 2H), 2.99 (s, 3H), 2.92–2.97 (m, 4H), 2.81 (s, 2H), 1.89 (q, J=7.5 Hz, 2H), 1.81–1.84 (m, 2H), 0.82 (t, J=7.5 Hz, 3H); MS (M+1) 452.3.

(+)-Exo-N-{3-[6-Ethyl-3-(2-hydroxy-1,2,3,4-tetrahydro-naphthalen-2-ylmethyl)-3-aza-bicyclo[3.1.0]hex-6-yl]-phenyl}-methanesulfonamide MS (M+1) 441.3; [α]$_D$+3.91° (c 1.04, MeOH).

(−)-Exo-N{3-[6-Ethyl-3-(2-hydroxy-1,2,3,4-tetrahydro-naphthalen-2-ylmethyl)-3-aza-bicyclo[3.1.0]hex-6-yl]-phenyl}-methanesulfonamide MS (M+1) 441.3; [α]$_D$−5.04° (c 1.07, MeOH).

(+/−)-Exo-N-(3-{6-Ethyl-3-[2-hydroxy-3-(2-hydroxy-indan-2-yl)-propyl]-3-aza-bicyclo[3.1.0]hex-6-yl}-phenyl)-methanesulfonamide 400 MHz $^1$H NMR (CDCl$_3$) δ 7.08–7.22 (m, 6H), 7.01–7.03 (m, 2H), 4.08–4.13 (m, 1H), 3.23–3.27 (m, 1H), 3.06–3.10 (m, 5H), 2.96–2.98 (m, 2H), 2.94 (s, 3H), 2.66–2.69 (m, 1H), 2.55–2.59 (m, 1H), 1.74–1.89 (m, 6H), 0.79 (t, J=7.5 Hz, 3H); MS (M+1) 471.2.

Exo-3-[3-(2-Hydroxy-indan-2-ylmethyl)-6-propyl-3-aza-bicyclo[3.1.0]hex-6-yl]-benzamide 400 MHz $^1$H NMR (CD$_3$OD) δ 7.78–7.79 (m, 1H), 7.64–7.67 (m, 1H), 7.44–7.46 (m, 1H), 7.33–7.36 (m, 1H), 7.09–7.17 (m, 4H), 3.23–3.29 (m, 2H), 3.12 (d, J=16.2 Hz, 2H), 2.99–3.02 (m, 2H), 2.89 (d, J=16.2 Hz, 2H), 2.75 (s, 2H), 1.95–1.99 (m, 2H), 1.81–1.85 (m, 2H), 1.21–1.29 (m, 2H), 0.83 (t, J=7.5 Hz, 3H); MS (M+1) 391.3.

Exo-N-{3-[3-(2-Hydroxy-indan-2-ylmethyl)-6-propyl-3-aza-bicyclo[3.1.0]hex-6-yl]-phenyl}-methanesulfonamide 400 MHz $^1$H NMR (CDCl$_3$) δ 7.00–7.24 (m, 8H), 3.19–3.22 (m, 2H), 3.03–3.14 (m, 2H), 2.98 (s, 4H), 2.96 (s, 3H), 2.83 (s, 2H), 1.79–1.83 (m, 4H), 1.19–1.26 (m, 2H), 0.83 (t, J=7.5 Hz, 3H); MS (M+1) 441.2.

Exo-2-Methoxy-ethanesulfonic acid (3-[3-(2-hydroxy-indan-2-ylmethyl)-6-propyl-3-aza-bicyclo[3.1.0]hex-6-yl]-phenyl}-amide 400 MHz $^1$H NMR (CDCl$_3$) δ 7.00–7.22 (m, 8H), 3.80 (t, J=5.4 Hz, 2H), 3.38 (s, 3H), 3.19–3.22 (m, 4H), 3.02–3.07 (m, 2H), 2.98 (s, 4H), 2.81 (s, 2H), 1.80–1.84 (s, 4H), 1.21–1.27 (m, 2H), 0.82 (t, J=7.5 Hz, 3H); MS (M+1) 485.3.

Exo-N-{3-[3-(2-Hydroxy-indan-2-ylmethyl)-6-isopropyl-3-aza-bicyclo[3.1.0]hex-6-yl]-phenyl}-methanesulfonamide 400 MHz $^1$H NMR (CDCl$_3$) δ 7.01–7.22 (m, 8H), 3.13–3.20 (m, 4H), 2.93–2.99 (m, 7H), 2.85 (s, 2H), 2.14–2.18 (m, 1H), 1.89 (s, 2H), 0.84 (d, J=7.1 Hz, 6H); MS (M+1) 441.2.

Exo-2-Methoxy-ethanesulfonic acid {3-[3-(2-hydroxy-indan-2-ylmethyl)-6-isopropyl-3-aza-bicyclo[3.1.0]hex-6-yl]-phenyl}-amide 400 MHz $^1$H NMR (CDCl$_3$) δ 7.03–7.21 (m, 8H), 3.80 (t, J=5.4 Hz, 2H), 3.39 (s, 3H), 3.13–3.38 (m, 6H), 2.99 (s, 4H), 2.85 (s, 2H), 2.08–2.18 (m, 1H), 1.90 (s, 2H), 0.84 (d, J=6.6 Hz, 6H); MS (M+1) 485.3.

Exo-Ethanesulfonic acid {3-[6-ethyl-3-(2-hydroxy-indan-2-ylmethyl)-3-aza-bicyclo[3.1.0]hex-6-yl]-phenyl}-amide 400 MHz $^1$H NMR (CDCl$_3$) δ 7.04–7.28 (m, 8H), 4.16–4.21 (m, 2H), 3.54 (s, 2H), 3.02–3.20 (m, 8H), 2.66 (s, 3H), 2.32 (m, 2H), 1.79 (q, J=7.5 Hz, 2H), 1.26 (t, J=7.5 Hz, 3H), 0.85 (t, J=7.5, 3H); MS (M+1) 441.6.

Example 9

Alternative General Procedure For the Preparation of Compounds of Formula (XXIII)

To a stirring solution of 1.0 equivalent of a compound of formula (XVIII) in anhydrous THF (0.1 M) at room temperature, was added Et$_3$N (5.0 equiv.) or pyridine (5.0 equiv.) and an appropriately substituted acid chloride (2.0 equiv.) of formula (XXIV). After stirring up to 24 hours, the reaction was quenched by the addition of saturated NaHCO₃ and diluted with methylene chloride. The layers were separated, the aqueous layer was extracted with methylene chloride and the combined organic layers were dried over anhydrous MgSO₄ and concentrated. The resulting crude material was used in the next step without purification.

To a stirring solution of 1.0 equivalent of the amide prepared above in THF (0.2M) at room temperature was added lithium aluminum hydride (4.0 equiv.). The resulting mixture was heated to 70° C. for up to 5 hours and then cooled to room temperature. The reaction was carefully quenched by the slow addition of a 1:1 mixture of Na₂SO₄.10 H₂O/Celite. The resulting slurry was stirred at room temperature for up to 16 hours. The slurry was diluted with THF and filtered through a celite pad, and the pad was washed several times with a 9:1 CH₂Cl₂/MeOH solution. The resulting solution was concentrated to yield crude material that was purified by flash chromatography to afford the desired tertiary amines of formula (XXIII) in 40–80% yield.

The following compounds were made using the above procedure of Example 9, starting with the appropriate starting amine of formula (XVIII) and the appropriate acid chloride reagent of formula (XXIV).

Furthermore, pharmaceutically acetable salts of the compounds listed below can be prepared as follows. To a stirring solution of compounds of the general formula (XXIII) (prepared as described above in Example 9, 1.0 equiv.) in a suitable solvent such as methyl ethyl ketone, methylene chloride/methanol (1:1) or methanol (0.1 M) at room temperature was added the appropriate acid, such as citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

Exo-2-Methoxy-ethanesulfonic acid [3-(6-ethyl-3-indan-2-ylmethyl-3-aza-bicyclo[3.1.0]hex-6-yl)-phenyl]-amide 400 MHz ¹H NMR (CDCl₃) δ 7.11–7.22 (m, 7H), 7.01–7.10 (m, 1H), 3.79–3.82 (m, 2H), 3.39 (s, 3H), 3.19–3.22 (m, 2H), 2.99–3.05 (m, 4H), 2.50–2.79 (m, 7H), 1.97–2.02 (m, 2H), 1.75 (m, 2H), 0.840 (t, J=7.4, 3H); MS (m+1) 455.1

Exo-3-(6-Ethyl-3-indan-2-ylmethyl-3-aza-bicyclo [3.1.0]hex-6-yl)-benzamide

400 MHz ¹H NMR (CD₃OD) δ 7.77–7.78 (m, 1H), 7.63–7.66 (m, 1H), 7.42–7.45 (m, 1H), 7.32–7.35 (m, 1H), 7.11–7.13 (m, 2H), 7.03–7.06 (m, 2H), 2.97–3.08 (m, 4H), 2.84–2.87 (m, 2H), 2.56–2.66 (m, 2H, 2.49–2.50 (m, 2H), 2.02–2.07 (m, 2H), 1.83–1.84 (m, 2H), 0.80–0.87 (m, 3H); MS (m+1) 361.2

Exo-1-Methyl-1H-imidazole-4-sulfonic acid [3-(6-ethyl-3-indan-2-ylmethyl-3-aza-bicyclo[3.1.0]hex-6-yl)-phenyl]-amide 400 MHz ¹H NMR (CD₃OD) δ 7.65 (s, 1H), 7.55 (s, 1H), 7.03–7.15 (m, 5H), 6.97–6.80 (m, 1H), 6.92–6.94 (m, 2H), 3.65 (s, 3H), 2.95–3.18 (m, 4H), 2.82–2.84 (m, 2H), 2.52–2.65 (m, 3H), 2.47–2.49 (m, 2H), 1.90–1.96 (m, 2H), 1.70–1.71 (m, 2H), 0.72 (t, J=7.4, 3H); MS (m+1) 477.1.

Exo-3-(6-Ethyl-3-indan-2-ylmethyl-3-aza-bicyclo [3.1.0]hex-6-yl)-phenol

400 MHz ¹H NMR (CDCl₃) δ 7.16–7.20 (m, 2H), 7.07–7.15 (m, 3H), 6.78–6.80 (m, 1H), 6.72–6.72 (m, 1H), 6.60–6.63 (m, 1H), 3.00–3.07 (m, 2H), 2.87–2.95 (m, 4H), 2.59–2.75 (m, 3H), 2.51–2.58 (m, 2H), 1.91–2.03 (m, 2H), 1.75–11.79 (m, 2H), 0.83 (t, J=7.4, 3H); MS (m+1) 334.2.

Exo-3-[6-Ethyl-3-(2-indan-2-yl-ethyl)-3-aza-bicyclo [3.1.0]hex-6-yl]-benzamide

400 MHz ¹H NMR (CDCl₃) δ 7.72 (s, 1H), 7.54–7.56 (m, 1H), 7.32–7.39 (m, 1H), 7.28–7.30 (m, 1H), 7.08–7.16 (m, 4H), 6.14 (brs, 1H), 5.79 (brs, 1H), 3.02–3.05 (m, 4H), 2.90–3.00 (m, 2H), 2.55–2.61 (m, 4H), 2.42–2.48 (m,1H), 1.89–1.92 (m, 2H), 1.83 (s, 2H), 1.67 (q, J=7.5 Hz, 2H), 0.77 (t, J=7.5 Hz, 3H); MS (M+1) 375.2.

What is claimed is:
1. A compound Formula (II)

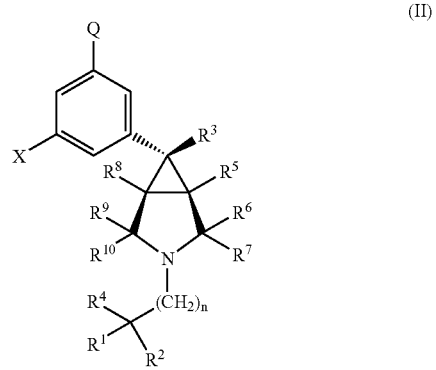

wherein
X is H, halogen or —CN;
Q is —OH, —C(=O)NH₂, or —NHS(=O)₂R¹¹;
R¹ and R² are, with the carbon to which they are attached, connected to form a C₅–C₆ cycloalkyl wherein said cycloalkyl is fused to a C₆ aryl;
R³ is C₂–C₃ alkyl;
R⁴ is —OH;
R5 and R8 are each independently H or methyl;
R⁶, R⁷, R⁹ and R¹⁰ are H;
R¹¹ is selected from the group consisting of C₁–C₄ alkyl, and —(C₂–C₄ alkylene)—O—(C₁–C₄ alkyl);
n is an integer selected from the group consisting of zero, 1, 2, and 3;
or a pharmaceutically acceptable salt thereof.
2. The compound of claim 1 selected from the group consisting of
Exo-N-(3-{6-ethyl-3-[2-(2-hydroxy-indan-2-yl)-ethyl]-3-aza-bicyclo[3.1.0]hex-6-yl}-phenyl)-methanesulfonamide;
Exo-3-{6-ethyl-3-[2-(2-hydroxy-indan-2-yl)-ethyl]-3-aza-bicyclo[3.1.0]hex-6-yl}-benzamide;
Exo-3-[6-ethyl-3-(2-hydroxy-indan-2-ylmethyl)-3-aza-bicyclo[3.1.0]hex-6-yl]-5-fluoro-benzamide;

Exo-N-{3-[6-ethyl-3-(2-hydroxy-indan-2-ylmethyl)-3-aza-bicyclo[3.1.0]hex-6-yl]-phenyl}-methanesulfonamide;

Exo-3-[6-ethyl-3-(2-hydroxy-indan-2-ylmethyl)-3-aza-bicyclo[3.1.0]hex-6-yl]-benzamide;

Exo-2methoxy-ethanesulfonic acid {3-[6-ethyl-3-(2-hydroxy-indan2-ylmethyl)-3-aza-bicyclo[3.1.0]hex-6-yl]-phenyl}-amide;

Exo-N-{3-[6-ethyl-3-(2-hydroxy-indan-2-ylmethyl)-3-aza-bicyclo[3.1.0]hex-6-yl]-5-fluoro-phenyl}-methanesulfonamide;

Exo-2-[6-ethyl-6-(hydroxy-phenyl)-3-aza-bicyclo[3.1.0.]hex-3-ylmethyl]-indan-2-ol;

(+/−)-Exo-N-{3-[6-ethyl-3-(2-hydroxy-1,2,3,4-tetrahydro-naphthalen-2-ylmethyl)-3-aza-bicyclo[3.1.0]hex-6-yl]-phenyl}-methanesulfonamide;

Exo-2methoxy-ethanesulfonic acid {3-[6-ethyl-3-(2hydroxy-1,2,3,4-tetrahydro-naphthalene-2-ylmethyl)3-aza-bicyclo[3.1.0]hex-6-yl]-phenyl}-amide;

(+/−)-Exo-3-[6-ethyl-3-(2-hydroxy-1,2,3,4-tetrahydro-naphthalen-2-ylmethyl)-3-aza-bicyclo[3.1.0.]hex-6-yl]-benzamide;

Exo-N-{3-cyano-5-[6-ethyl-3-(2-hydroxy-indan-2-ylmethyl)-3-aza-bicyclo[3.1.0]hex-6-yl]-phenyl}-methanesulfonamide;

(+)-Exo-N-{3-[6-ethyl-3-(2-hydroxy-1,2,3,4-tetrahydro-naphthalen-2-ylmethyl)-3-aza-bicyclo[3.1.0]hex-6-yl]-phenyl}-methanesulfonamide;

(−)-Exo-N-{3-[6-ethyl-3-(2-hydroxy-1,2,3,4-tetrahydro-naphthalen-2-ylmethyl)-3-aza-bicyclo[3.1.0]hex-6-yl]-phenyl}-methanesulfonamide;

Exo-3-[3-(2-hydroxy-indan-2-ylmethyl)-6-propyl-3-aza-bicyclo[3.1.0]hex-6-yl]-benzamide;

Exo-N-{3-[3-(2-hydroxy-indan-2-ylmethyl)-6-propyl-3-aza-bicyclo[3.1.0]hex-6-yl]-phenyl}-methanesulfonamide;

Exo-2methoxy-ethanesulfonic acid {3-[3-(2-hydroxy-indan-2-ylmethyl)-6-propyl-3-aza-bicyclo[3.1.0]hex-6-yl]-phenyl}-amide;

Exo-N-{3-[3-(2-hydroxy-indan-2-ylmethyl)-6-isopropyl-3-aza-bicyclo[3.1.0]hex-6-yl]-phenyl}-methanesulfonamide;

Exo-2-methoxy-ethanesulfonic acid {3-[3-(2-hydroxy-indan-2-ylmethyl)-6-isopropyl-3-aza-bicyclo[3.1.0]hex-6-yl]-phenyl}-amide; and Exo-ethanesulfonic acid {3-[6-ethyl-3-(2-hydroxy-indan-2-ylmethyl)-3-aza-bicyclo[3.1.0]hex-6-yl]-phenyl}-amide;

or a pharmaceutically acceptable salt thereof.

3. The compound of claim 1 wherein

X is H;

Q is —NHS(=O)$_2$R$^{11}$;

R$^1$ and R$^2$ are, with the carbon to which they are attached, connected to form a C$_5$–C$_6$ cycloalkyl wherein said cycloalkyl is fused to a C$_6$ aryl;

R$^3$ is ethyl;

R$^6$, R$^7$, R$^9$ and R$^{10}$ are H;

R$^{11}$ is C$_1$–C$_4$ alkyl; and n is 1;

or a pharmaceutically acceptable salt thereof.

4. The compound of claim 3 wherein R$^1$ and R$^2$ are, with the carbon to which they are attached, connected to form a C$_5$ cycloalkyl fused to a C$_6$ aryl;

or a pharmaceutically acceptable salt thereof.

5. The compound of claim 4 which is exo-N-{3-[6-ethyl-3-(2-hydroxy-indan-2-ylmethyl)-3-aza-bicyclo[3.1.0]hex-6-yl]-phenyl}-methanesulfonamide;

or a pharmaceutically acceptable salt thereof.

6. The compound of claim 5 wherein said pharmaceutically acceptable salt is mesylate.

7. A pharmaceutical composition comprising a compound of claim 1 or a pharmaceutically acceptable salt thereof and a pharmaceutically acceptable carrier.

8. The pharmaceutical composition of claim 7 wherein said compound is exo-N-{3-[6-ethyl-3-(2-hydroxy-indan-2-ylmethyl)-3-aza-bicyclo[3.1.0]hex-6-yl]-phenyl}-methanesulfonamide or the mesylate salt thereof.

* * * * *